-continued

Effects of Cyclichexapeptide Analogs of Somatostatin on Gastric Secretion
(Dose 0.8 g/ml./min. - infusion 0-60 min.)

Gastric Secretion & Inhibition

| Compound | Vol. | | | | Acid Concentration | | | | Dose |
|---|---|---|---|---|---|---|---|---|---|
| | 0-30 | 30-60 | 60-90 | 90-120 | 0-30 | 30-60 | 60-90 | 90-120 | |
| Cyclo(Pro—Phe—D-Trp—cisACHxAla—Thr—Phe) | 75 | 82 | 20 | 2 | 4 | 19 | 13 | 5 | 0.8 |

What is claimed is:

1. A compound having the formula:

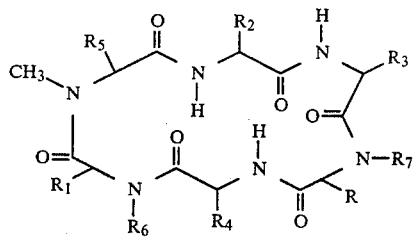  I and

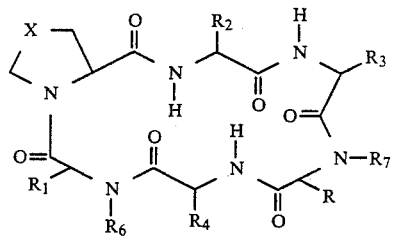  II wherein
R is

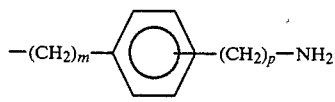

such that the broken line indicates that the ring may be either cyclohexyl or phenyl;
m is 0 or 1; and p is 0 when the ring is cyclohexyl and 1 when the ring is phenyl;
X is $(CH_2)_n$ wherein n is 0, 1 or 2, sulfur;
$R_1$ and $R_2$ are independently lower alkyl, benzyl, substituted benzyl wherein the substituent may be one or two of loweralkyl, halogen, hydroxy, amino, nitro or loweralkoxy; and loweralkyl substituted with hydroxy, 3-indolylmethyl, carboxy, amino, guanidino, or a 5- or 6-membered heterocyclic ring;
$R_3$ is 3-indolylmethyl or substituted 3-indolylmethyl wherein the substituent may be loweralkyl, loweralkoxy or halogen;
$R_4$ is loweralkyl, hydroxyloweralkyl, benzyl, carboxyloweralkyl, aminoloweralkyl, 3-indolylmethyl or substituted hydroxy benzyl wherein the substituent may be loweralkyl, loweralkoxy, hydroxy, halogen, amino or nitro, or a 5- or 6-membered heterocyclic ring;
$R_5$ is loweralkyl, benzyl, or substituted benzyl wherein the substituent is loweralkyl, loweralkoxy, hydroxy, halogen, amino or nitro; and
$R_6$ and $R_7$ are independently hydrogen or methyl.

2. A compound of claim 1 wherein:
X is $(CH_2)_n$ and n is 1;
$R_1$ and $R_2$ are as defined in claim 1;
$R_3$ is 3-indolylmethyl or substituted indolylmethyl wherein the substituent is methoxy or fluoro;
$R_4$ is methyl, ethyl, hydroxymethyl or hydroxyethyl; and
$R_5$ is methyl
$R_6$ and $R_7$ are hydrogen.

3. A compound of claim 2 wherein:
X and Y are methylene;
$R_1$ and $R_2$ are as defined in claim 1
$R_3$ is 3-indolylmethyl;
$R_4$ is hydroxyethyl; and
$R_5$ is methyl
$R_6$ and $R_7$ are hydrogen.

4. The compound of claim 2 which is cyclo (Pro-Tyr-D-Trp-t-4-AchxAla-Thr-Phe).

5. The compound of claim 2 which is cyclo (Pro-Phe-D-Trp-t-4-AchxAla-Thr-Phe).

6. The compound of claim 2 which is cyclo (N-Me-Ala-Tyr-D-Trp-t-4-AchxAla-Thr-Phe).

7. The compound of claim 2 which is cyclo (Pro-Tyr-D-Trp-4-Amphe-Thr-Phe).

8. The compound of claim 2 which is cyclo (Pro-Phe-D-Trp-4-Amphe-Thr-Phe).

9. The compound of claim 2 which is cyclo (N-Me-Ala-Tyr-D-Trp-t-4-Amphe-Thr-Phe).

10. A method for inhibiting the release of growth hormone, glucagon or insulin which comprises administering to an animal an effective amount of a cyclic hexapeptide of claim 1.

11. A pharmaceutical composition useful for inhibiting the release of growth hormone, glucagon or insulin comprising a therapeutically effective amount of the cyclic hexapeptide of claim 1 or the non-toxic acid addition salts, thereof in a pharmaceutically acceptable liquid or solid carrier.

* * * * *

United States Patent [19]

Nonomura et al.

[11] Patent Number: 4,522,814

[45] Date of Patent: Jun. 11, 1985

[54] **COMPOSITION OF MATTER FROM *CRYPTOSIPHONIA WOODII* USEFUL FOR THE TREATMENT OF HERPES SIMPLEX VIRUS**

[75] Inventors: Arthur M. Nonomura, San Francisco, Calif.; Raphael Pappo, 913 Cambridge Ave., Redwood City, Calif. 94061

[73] Assignee: Raphael Pappo, Redwood City, Calif.

[21] Appl. No.: 439,369

[22] Filed: Nov. 5, 1982

[51] Int. Cl.$^3$ .................... A61K 31/715; C08B 37/00
[52] U.S. Cl. ....................................... 514/54; 536/1.1; 536/123
[58] Field of Search ................. 536/1.1, 123; 424/180

[56] References Cited

U.S. PATENT DOCUMENTS 4,229,440  10/1980  Murofushi et al. ................. 536/123

OTHER PUBLICATIONS

Hatch et al., "Chem. Abst." vol. 92, 1980, p. 69621(v).

*Primary Examiner*—Johnnie R. Brown
*Attorney, Agent, or Firm*—John P. White

[57] ABSTRACT

A water extract of homogenized *Cryptosiphonia woodii* is useful for the treatment of herpes simplex viral infections. The active agent in the extract is a polysaccharide containing glucose and galactose.

Herpes infections may be treated in subjects, e.g. human patients, by administering to the subject an effective amount of an aqueous extract of *C. woodii*, particularly a water extract. This treatment method is effective for treating subjects both prior to and subsequent to infection. It may involve topical application to alleviate symptoms associated with herpes infections or desirably may be systemic, e.g. by oral administration, to eradicate the virus and thereby prevent symptom recurrence.

14 Claims, No Drawings

COMPOSITION OF MATTER FROM *CRYPTOSIPHONIA WOODII* USEFUL FOR THE TREATMENT OF HERPES SIMPLEX VIRUS

BACKGROUND OF THE INVENTION

Crude preparations from species in the Dumontiaceae extracted in citrate phosphate buffer when added to cell cultures or mice prior to or simultaneous with inoculation by herpes simplex virus have been reported to inhibit herpes simplex virus, but when cells or animals were treated after inoculation with herpes simplex virus, no significant inhibition of the virus infection was observed (Deig, et al. 1974: Ehresmann, et al. 9175; Hatch, et al. 1977; Deig, et al. 1977; Ehresmann, et al. 1977; Richards, et al. 1978; Deig, et al. 1979; Hatch, et al. 1979; Ehresmann, et al. 1979). Results given in this present disclosure show improvement by extraction with water. We also show that, contrary to the findings cited in the above literature, treatment of cell cultures or of animals with aqueous extracts of algae two hours after inoculation with herpes simplex virus inhibits the virus infection. Additionally, contrary to results given by Deig, et al. 1974, the present finding is that acetone and chloroform solvent extracts from *Cryptosiphonia woodii* have anti-herpes activity as shown in in vitro assays.

The water extraction is different from previously known methods since no buffering salts were added. Water extracts have a pH 4.5 to pH 5.5 during the first extraction of the alga. All previous extractions from *Cryptosiphonia woodii* cited in the above literature have been made in a pH 7.0 citrate phosphate buffer. This is essentially an alkaline buffer at pH 7 and it will extract any organic acids including those of high molecular weight. Simple water extracts result in solutions of pH 4.5 to pH 5.5 which could contain acid soluble bases. This chemical difference is corroborated by the biological differences found. For instance, the citrate phosphate buffered extract of *Crytosiphonia woodii* was cited by Deig, et al (1974) as blocking cell receptor cites indicating a lack of post-infective activity in vitro against herpes simplex virus. In later publications (Richards, et al 1978; Hatch, et al 1979), it was concluded that algal extracts has inhibitory value against herpes simplex virus only if cell monolayers or mice were treated with extracts prior to infection. In contrast, our findings show that water extracts from *Cryptosiphonia woodii* inhibit herpes simplex virus when applied after infection of cell monolayer cultures.

Previously, mouse in vivo assays of preparations from *Farlowia mollis* (Richards, et al. 1978), and *Cryptosiphonia woodii* (Hatch, et al. 1979) showed prophylactic, but no therapeutic antiviral efficacy. In our hands, the antiviral extract from *Cryptosiphonia woodii* described herein shows therapeutic value in vivo by decreasing intravaginal herpetic lesions in guinea pig assays when applied after virus infection.

In their attempts to characterize the active component in *Constantinea simplex* (Hatch, et al. 1979), *Cryptosiphonia woodii*, and *Farlowia mollis* (Deig, et al. 1974), previous researchers suggested that a polysaccharide or glycoprotein was involved, however, the antiviral compound was not isolated. Participation of a protein was suggested based on heat lability and on observed decrease of in vitro activity when *C. simplex* extracts were treated with proteolytic enzymes (Hatch et al. 1979). In this report, we shall disclose the results of purifications of extracts from *C. woodii* and assays of some of the fractions in vitro which lead us to conclude that a polysaccharide (with glucose and galactose units) is the active component. Results also given in the present disclosure show that in the in vivo guinea pig vaginitis model, the whole aqueous extracts derived from *Cryptosiphonia woodii* are active on post-infection treatment.

SUMMARY OF THE INVENTION

A water extract of homogenized *Cryptosiphonia woodii* is useful for the treatment of herpes simplex virus infections. The active agent included in the extract is a polysaccharide containing glucose and galactose.

Herpes simplex viral infections may be treated in a subject, particularly in a human patient, by administering to the subject an effective amount of an aqueous extract of *C. woodii*, particularly a water extract. This treatment method is effective for treating subjects both prior to and subsequent to infection. The method of treatment may involve topical application to alleviate symptoms associated with herpes infections. Desirably the treatment may be systemic, e.g. by oral administration, to eradicate the virus and thereby prevent symptom recurrence.

DETAILED DESCRIPTION OF THE INVENTION

Materials and Methods

General Description

*Cryptosiphonia woodii* commonly occurs as a saxicolous growth in the mid-tidal levels (+0.5 ft. to +1.5 ft. tide level) from Alaska to San Pedro, Calif. shores (Abbott and Hollenberg 1976). The specific alga is picked by hand from rocks exposed during low tide periods and placed in plastic bags or nylon net bags (Example 1). The collection is rinsed, drained, sorted and frozen. The algae are stored in freezing compartments at $-20°$ C., or may be freeze dried and stored at $4°$ C. until ready for use.

Portions of the algal collection are processed for the antiviral compound first by homogenization. Thorough homogenization is important for extraction of optimal quantities of active components. Several methods have proven useful including pulverization in liquid nitrogen (Example 2), aqueous homogenization (Example 3), and dry grinding (Example 4).

After the alga is homogenized, the algal solution is brought to volume in aqueous solution or it is extracted in acetone or other solvents. The particulate matter is centrifuged or filtered off and the liquid supernatant is recovered as the crude aqueous or solvent extract.

The crude aqueous extract is purified to higher in vitro activity by using several methods which may be used sequentially for greater purification: ethanol fractionation (Example 5), membrane filtration (Example 6), protein denaturation (Example 7), protein digestion (Example 8), and quarternary ammonium salt precipitation (Example 9).

Chemical characterization of the antiviral compound was undertaken using several techniques and assayed in vitro. Molecular weight estimates were made by gel filtration (Example 10) and membrane exclusion (Example 11). Stability was tested in the presence of acid (Example 12) and base (Example 13) and in acid at $100°$ C. (Example 14). Heat stability at various temperatures was also assayed (Example 15). Oxidation with periodic acid was tested (Example 16). Separation by means of cation exchange chromatography (Example 17) was attempted.

General enzymes (Example 18) and specific enzymes (Example 19 through 29) were reacted with the algal extract in order to determine the specific components necessary for in vitro antiviral activity.

Antiviral activity was assayed in vitro using HSV-1 in a plaque assay on Vero monolayer cultures (Example 30). In vivo activity was assayed against guinea pig models (Example 31).

Elemental analyses of water extracts were made by Galbraith Laboratories (Table 31) for *Cryptosiphonia woodii.*

EXAMPLE 1

Collection and Storage of Raw Material

*Cryptosiphonia woodii* plants were collected from exposed rocks during the springs of 1981 and 1982 from Dillon Beach, Sonoma County, Calif. and Duxbury Reef, Marin County, Calif. The plants were rinsed in seawater and undesirable plants and animals were discarded. Healthy plants were drained of seawater and sealed in quart size Dow Zip Lock plastic bags. These samples were frozen over dry ice for transport to laboratory storage freezers at $-20°$ C.

800 grams of frozen algae were placed into two Labconco #75432 21 lyophilization flasks and freeze dried in a Virtis Freezemobile 12 lyophilizer for 24 hours. The dried resultant 106 grams of alga was sealed in a glass jar and stored at 4° C.

The remainder of the wet algae was stored frozen at $-20°$ C. until used.

PREPARATION OF CRUDE EXTRACTS

EXAMPLE 2

Pulverization in Liquid Nitrogen 800 grams frozen weight of *Cryptosiphonia woodii* from Dillon Beach, Sonoma County, Calif. were frozen on dry ice for 1 hour. The alga was removed from its plastic bag and placed in a deep stainless steel one gallon bucket with 200 ml liquid nitrogen. The alga was immersed in the liquid nitrogen and chilled for five minutes.

With numerous forceful swings at the frozen algal mass with a 2 pound Estwing Mfg. Co. steel sledge hammer, the alga was pulverized to a power in thirty minutes.

The frozen algal powder was stirred into 2 liters of 0.01M citrate phosphate buffer pH 6.5 with physiological saline (8.2 gm/l NaCl). The solution was allowed to extract for 48 hours. The algal particulates were separated from the viscous supernatant by centrifugation in 500 ml bottles for 1 hour at 4,800 rpm. The supernatant was poured off and small aliquots freeze dried. This crude first extract showed in vitro activity to 0.1 gm/ml concentration (Table 1, Sample 432-83 A and B).

The algal particulate pellet is resuspended in 1 liter of buffer as above, but with the addition of 1% Triton X-100. The solution is allowed to extract for 24 hours. The supernatant is collected by centrifugation and the algal particulate pellet is discarded. The Triton X-100 is removed by mixing the supernatant with excess Biobeads SM-2 (Biorad) for 1 minute. A 10 ml aliquot of the solution is sterile filtered through Nalgene 0.2u Type S units. The lyophilized extract showed in vitro activity to 0.01 mg/ml (Table 1, Sample Number 432-87 A through C). This extract also showed in vivo activity in the guinea pig vaginitis model (Table 22, Sample EP1008).

EXAMPLE 3

Water Extraction

To 2 liters of chilled (4° C.) water in a cooled base Waring 2610 CB 1 gallon container on an Eberbach 8017 Blender Power unit homogenizer cooled with attachment to a Lauda K-2 RD refrigerated circular, slowly add 1 kilogram of *Cryptosiphonia woodii* pulverized in liquid nitrogen as per Example 2. In this example, the 1 kilogram of powdered algae is added in 3 homogenizations lasting a total of 10 minutes. The solution is then homogenized further for 5 to 10 minutes maintaining the temperature below 15° C. Depending on the efficiency of the refrigeration unit, the homogenization may be accomplished in a single constant run or in 2 to 4 minute pulses with cooling intervals of 30 minutes. The crude homogenate is transferred in 350 ml aliquots to a 500 ml standard fluted Virtis (6513-0405) microflask and homogenized with a Virtis 60K homogenizer at 20,000 rpm with the Macro Ultra Shear blade for 1 minute. The resultant viscous homogenate is then set to extract at 4° C.

The algal homogenate solution is placed in a large beaker on a Corning PC 101 magnetic stirring table and stirred at medium speed with a VWR Bel-Art $3 \times \frac{1}{2}$ inch spinbar for 24 hours at 4° C. The solution is kept cool through all extractions in order to reduce growth of contaminants. The particulates are separated from the aqueous extract by centrifugation. 300 ml aliquots of the algal solution are placed in 500 ml centrifuge bottles. These are spun at 4° C. for 30 minutes at 5,000 rpm in a Sorval RC 2 preparative refrigerated centrifuge.

The first supernatant is poured off and saved and the pellets of algal particulates are transferred with a spatula to a large beaker for further extraction.

The algal pellet is resuspended in 7 liters of water. The solution is extracted overnight with stirring. The aqueous extract is separated from the algal particulates by centrifugation. The supernatant is saved and the pellet is extracted a third time by the same process. The third extract from the same algal pellet shows higher activity (Table 20, Sample 462-10 C) than first or second extracts (Table 20, Sample 462-10 A, 462-10 B, 462-28 A, 462-28 B) in in vitro assay.

EXAMPLE 4

Homogenization by Dry Grinding and Solvent Extraction 106 grams of freeze dried *Cryptosiphonia woodii* is ground to powder using a large Coors 60328 mortar and Coors 60329 pestle. The dry powder is stirred in 1000 ml of acetone for 24 hours. The green acetone supernatant is filtered off over a sintered glass funnel with vacuum aspiration. The acetone extraction is repeated twice. The alga is stirred into 100% ethanol 1000 ml for 2 hours. The ethanol is filtered off. The ethanol extraction is repeated three times. The alga is finally stirred into 250 ml of ether and is extracted for 1 hour. The ether is filtered off and the algal powder is dried in vacuo for 12 hours. One liter of chloroform may be substituted for the ethanol and ether treatments on extraction overnight. The chloroform must be collected by filtration over a sintered glass funnel and the alga dried in vacuo. All solvent extracts are saved and the solvents evaporated off in a Buchi Rotovap, the resultant solvent extracts weighing approximately 0.6 to 1.0 gram. The solvent extracts showed in vitro activity with acetone extracts (Table 18, Samples 374-95 and 462-63) showing less in vitro activity than the chloroform extract (Table 18, Sample 462-66).

The solvent extracted dry algal powder is stirred into 2000 ml pH 2.2 0.01M citric acid with 2N NaCl with stirring at 4° C. for extraction. The solution is allowed to extract for 48 hours and then centrifuged to separate the aqueous extract from the particulates. The supernatant is dialyzed in Spectrapor 6 tubing and lyophilized resulting in 3.5 gm dried material per 100 ml. The lyophilized aqueous extract was active in vitro above 0.1 mg/ml (Table 15 Sample 374-56 A) and showed numerous protein staining bands on polyacrylamide gel electrophoresis. Aqueous extracts from dried algae treated with solvents as for Example 4 showed no in vivo activity (Table 27, Samples EP 1025-EP 1028).

The particulate algal pellet that had been solvent and aqueous extracted was resuspended in 2 liters of water with 2.5N NaCl, 0.5N $CaCl_2$, and 1% Triton X-100 at pH 4.2. After three days extraction, the supernatant was recovered and the pellet discarded after centrifugation. A 100 ml aliquot was treated with Biobeads SM-2 for removal of Triton X-100 and then dialyzed in Spectrapor 6 tubing for 24 hours in running tap water. The sample was lyophilized and weighed 0.51 gm/100 ml. This second extract was active in vitro at 0.1 mg/ml (Table 16, Sample 374-57 C).

EXAMPLES 5-9

Purification

The crude extracts of *Cryptosiphonia woodii* taken from Examples 2,3 or 4 are the starting materials for polysaccharide purification for higher in vitro activity. The purification methods may be used sequentially.

EXAMPLE 5

Purification by Ethanol Precipitation

One liter of water extract prepared as for Example 3, but with 2N NaCl is placed in a 2 liter screw cap Erlenmeyer flask and chilled over ice for 1 hour. The chilled extract is placed on a Corning 8120 stirring plate and is stirred by a VWR Bel Art 3×½ inch spinbar at high speed. 500 ml of 0° C. chilled 200 proof Punctilious Ethanol is added to the extract slowly with rapid stirring. The solution is stirred for one hour at 4° C. Stirring is stopped and the precipitate is allowed to settle or float to the surface. Floating precipitate is pulled out of the vessel with 10 inch long forceps and drained in a stainless steel 3 inch Ecko brand kitchen strainer. The remainder of the solution is centrifuged for 30 minutes at 5,000 rpm. The supernatant is discarded. The pelleted precipitate is collected and dried in vacuo for 24 hours.

Purified ethanol precipitates of algal crude extracts showed activity to 0.01 mg/ml (Table 7, Samples 374-18 A, B, C; Table 8, 34 N, O; Table 10, 37 U, V; Table 12, 40 O, P). The ethanol precipitate of non-buffered extract showed activity on assays in vivo (Table 21, Sample EP 1013).

EXAMPLE 6

300,000 MW Filtration

One gram of lyophilized algal extract is dissolved in 100 ml sterile water. Dissolution of the preparation is facilitated by adding the powder to the water slowly with stirring, and continuously stirring the solution overnight.

The solution is transferred to an Amicon 202 stirred cell with an Amicon XM dialysis membrane filter of appropriate porosity (XM 300, XM 100, or XM 50). Five columns of water are passed through the solution in dialysis under 40 psi $N_2$ gas pressure. The dialysis filtrate and retentate solution are shell frozen and lyophilized.

in vitro activity was retained by membrane filters with 300,000 MW porosities for globular proteins (Table 10, Samples 374-37 I, J). Somewhat lower in vitro activity was observed in the fraction less than 300,000 MW, but greater than 100,000 MW, (374-37 K and L) and no activity was observed in the fraction below 100,000 MW (Table 10, Samples 374-37 M and N). No in vivo activity was observed in the sample retained by Amicon XM 300 membranes (Table 24, Sample EP 1021) although it was derived from active Sample EP 1012 (Table 21) which is an ethanol precipitate of a non-buffered extract in high salt concentration. In contrast, the XM 300 membrane retentate of a crude buffered extract (Sample EP 1032, Table 29) showed activity (Sample EP 1035, Table 30) and the filtrate was not active (Sample EP 1036, Table 30).

EXAMPLE 7

Protein Denaturation

One gram of dried algal extract prepared from Example 4 by solvent extraction is dissolved in 100 ml water by stirring for 2 hours at 37° C.

To the dissolved algal solution, an equal volume of 10% trichloracetic acid is slowly stirred in. The solution is allowed to react for 1 hour.

The solution is transferred to 10 Nalge 3111 Tefzel centrifuge tubes and spun at 20,000 rpm for 20 minutes. The supernatant is collected and the pellet discarded. To the supernatant, 2N NaCl is added. One half volume of ethanol is gradually stirred into the solution. The resultant precipitate is collected and washed with 500 ml 80% ethanol. The precipitate is resuspended in 50 ml water and dialyzed in Spectrapor 6 50,000 MW tubing in 4 l distilled water. The solution is lyophilized and yields 460 mg dried sample with in vitro activity (Table 16, Sample 374-61 A), but no in vivo activity (Table 27, Sample EP 1028).

EXAMPLE 8

Protein Denaturation and Enzyme Digestion

In 25 ml of water, 25 mg of the denatured lyophilized product from Example 7 is dissolved. The solution is warmed to 37° C. and adjusted to pH 7.5. One mg of Proteinase K (Boehringer Mannheim) is dissolved in 1 ml of water and then stirred into the algal solution. After four hours reaction at 37° C., the solution is placed in Spectropor 6 50,000 M.W. tubing and dialysed against running tap water overnight, followed by dialysis with 4 l distilled water for 4 hours. The solution is lyophilized, yielding 19 mg. This sample 374-76B (Table 17) showed high in vitro antiviral activity below 0.01 mg/ml and a similar plaque count (2 plaques) at 0.001 mg/ml to the TCA treated control (374-76A) which showed 6 plaques at 0.001 mg/ml.

Other preparations with protease (Sigma) followed by TCA denaturation (Table 16, 374-57E) showed virus inhibition similar to samples treated with protease (374-57F) or TCA (374-57G) alone when assayed in vitro.

Preparations in this example showed no in vivo activity (Table 28, Sample EC 1029).

EXAMPLE 9

Quarternary Ammonium Salts

All reactions in Example 4 are done in solutions warmed to 30° C. 10 grams of Sigma cetylpyridinium chloride (CPC) is dissolved in water to make a 1% solution. One gram of dry algal extract is dissolved in 500 ml water adjusted to pH 7. 500 ml of 1% CPC is added very slowly to the rapidly stirring algal solution. The final mixed solution is placed in a 30° C. warm water bath for 1 hour to insure completion of the reaction. The precipitate is collected by centrifugation at 2,000 rpm for 30 minutes. The supernatant is discarded and the pelleted precipitate is saved. The pellet is redissolved in 200 ml 2N NaCl in water at 37° C. The completely dissolved pellet is poured into 1 l chloroform. The biphasic mixture is placed on a magnetic stirrer in a refrigerator at 0°–4° C. The solution is stirred rapidly at 4° C. overnight to decomplex the polysaccharide of the quaternary ammonium salt. By use of a separatory funnel, the chloroform is removed and the polysaccharide solution is retained. 2 volumes of ethanol are slowly stirred into the polysaccharide solution. The precipitate is recovered by filtration on a sintered glass funnel. The precipitate is dissolved in water and dialyzed in Spectropor 6 50,000 MW tubing against 4 l distilled water for 4 hours. The solution was lyophilized and showed in vitro activity to 0.01–0.001 mg/ml (Table 17, 374-76J), but no in vivo activity (Tables 24 and 25, Sample EP 1023).

EXAMPLE 10

Characterization by Gel Filtration

A Pharmacia K 26/100 column with flow adaptors was packed to a 250 ml bed volume with Pharmacia Sephacryl S-200. The gel was equilbrated to pH 6.8 with 10 mM citrate phosphate buffer. Crude algal extract 20 mg was dissolved in 3 ml of the same buffer and applied to the column. The column ran at 1 ml/min flow rate and 15 ml fractions were collected using a Pharmacia Frac 300. Void volume was previously calibrated with blue dextran at 220 ml.

A active component was eluted within the void volume (Table 5, Sample 374-12 A). This accelerated movement suggests that a negatively charged polysaccharide was involved (Pigman, et al. 1980) in the inhibition of HSV-1 activity in vitro.

EXAMPLE 11

Characterization by Membrane Filtration

Amicon stirred cells Models 202 or 12 were used with XM 300, XM 100, XM 50, or PM10 Amicon Diaflow membranes. Nominal molecular weight cut-offs were 300,000; 100,000; 50,000; and 10,000 Daltons respectively. The stirred cell was assmembled beginning with the highest molecular weight membrane. An appropriate volume of algal extract was pipetted into the vessel, and 40-50 psi of Liquid Carbonic brand 99.99% nitrogen gas introduced a pressurized flow of distilled water into the stirred cell from an Amicon RS4 reservoir. The eluant was collected in a beaker. Aliquots of the eluants were saved and freeze dried for assay. The remainder of the eluant was membrane filtered sequentially through membranes of lower molecular weight cut-offs. Aliquots of each eluant were freeze dried and saved for assay. The retentate of the initially filtered extract was freeze dried for assay.

The highest in vitro activity in ethanol purified fractions from non-buffered extracts was retained by Amicon XM 300 membranes (see Table 10, Samples 374-37 I to N), but it did not show in vivo activity (Tables 24 and 25, Sample EP 1021). In contrast, the Amicon XM 300 membrane retentate of the buffered extract showed activity and the filtrate showed no activity (Table 30, Samples EP 1035 and EP 1036).

EXAMPLE 12

Stability in Strong Acid

Lyophilized algal extract that had been ethanol precipitated was dissolved into 1N HCl. The solution was left standing at room temperature for 5 days. The solution was then adjusted to pH 7 with the complement base and dialyzed against water.

Treatment with 1N HCl did not decrease in vitro activity (Table 9, Sample 374-35 G), but no in vivo activity was observed (Table 27, Sample EP 1027).

EXAMPLE 13

Stability in Base

Lyophilized algal extract that had been ethanol precipitated was dissolved into 1N NaOH. The solution was left standing at room temperature for 5 days. The solution was then adjusted to pH 7 with the complement acid and dialyzed against water.

Treatment with 1N NaOH decreased in vitro activity (Table 8, Sample 374-35 E) of the algal extract.

EXAMPLE 14

Stability in Strong Acid at 100° C.

A 1 mg/ml solution of algal extract in 1N HCl was prepared. Approximately 5 mls were placed in 10 ml glass ampuoles and sealed. These sealed ampuoles were placed in 100° C. ovens for 4 hours and 24 hours. Similar solutions were also prepared in 6N HCl and heated in a dry oven for 4 hours at 100° C. Solutions were normalized to pH 7 and sequentially filtered through Amicon XM 300, XM 100, and XM 50 membranes in stirred cells.

All in vitro activities in samples heated to 100° C. in strong acid were lost (see Tables 10 and 11, Samples 374-39 A to X).

A lower concentration of acid was used for a shorter time by dissolving 3 mg of the ethanol precipitate in 0.04N HCl at 100° C. for 2.5 hours. The sample was dialyzed against water and then concentrated to ⅓ the initial volume. One volume of ethanol was added with stirring. An additional volume of EtOH saturated with sodium acetate was added and the entire solution was refrigerated overnight at 5° C. The precipitate was centrifuged off. The solid precipitate was rinsed with EtOH several times, drained and then lyophilized. This sample showed loss of in vitro antiviral activity (Table 12, Samples 374-42 G, H and Table 11, Samples 374-40 E, F).

EXAMPLE 15

Heat Stability

Algal extracts in buffered solution, were placed in screw cap glass bottles and subjected to constant temperatures in a Blue M Magni Whirl constant temperature water bath. Extracts were heated to 25° C., 37° C., 50° C., 60° C., and 100° C. for 1 hour. Up to 60° C., no loss of in vitro activity was observed (Table 3, Samples 374-4 F to K and Table 6, Samples 374-17 J, K, L).

EXAMPLE 16

Periodate Treatment

A 1 mg/ml solution of the acetone precipitate was made in 2% periodic acid. The solution was left in the dark for 2 hours at room temperature. The reaction was stopped by addition of excess glucose. Half of the solution was treated with 1N NaOH to facilitate the elimination reaction for hydrolysis of the polysaccharide. The solutions were dialyzed and lyophilized for assay. These samples showed no significant change for in vitro antiviral activity (Tables 10, Samples 374-37 E, F, G and H).

EXAMPLE 17

Cation Exchange Chromatography

In order to determine the optimal pH for a column run, five mls of Pharmacia CM-Sepharose CL 6B (Lot No. FE 16087) cation exchanger (CMS) was poured as a slurry into each of five 10 cc Pharmaseal stylex syringe cylinders (sans plungers) plugged with a small (0.5 cc) wad of Pyrex 7220 glass wool. These CMS mini-columns were equilibrated to different pH's of 4, 5, 6, and 7 by running 10 mm Citrate Phosphate buffer at pH 4, 5, 6, and 7 through them at about 1 ml/minute for several hours. The mini-column eluant pH was checked by Schleicher and Schull Panpeha indicator paper for equilibration.

20 mls of crude extract that had been dialyzed against column buffers at pH 4, 5, 6, or 7 were run through corresponding columns.

Mini-columns were run at the same rate at room temperature. The 20 ml sample eluant plus a 10 ml wash was collected and dialyzed against pH 6.8 10 mM citrate phosphate buffer. Each column was eluted with 15 mls each of 50, 100, 500, and 1000 mm NaCl at the column pH. Each sample was dialyzed in pH 6.8 10 mM citrate phosphate buffer overnight and then 8 ml aliquots were lyophilized.

The optimal pH for chromatographic separation was determined at pH 5 to 6 (see Tables 3 and 4, Samples 374-6 through 374-8).

EXAMPLES 18–29

Enzyme Treatment

The following enzymes in Examples 18 through 29 were mixed with the ethanol precipitate of the algal extract in aqueous solution at a ratio of 1:50 w/w enzyme: algal extract. The pH and temperatures were adjusted to those listed for each enzyme and the reaction was maintained for 2 hours.

| Enzyme | Catalogue # | pH | Temperature |
| --- | --- | --- | --- |
| Protease | Sigma P5147 | 7.5 | 37° C. |
| Chymotrypsin | Sigma C4129 | 7.8 | 25° C. |
| β-xylosidase | Sigma X5375 | 5.0 | 25° C. |
| β-n-acetylglucosaminidase | Sigma A3015 | 4.0 | 25° C. |
| β-glucosidase | Sigma G8625 | 5.0 | 37° C. |
| β-galactosidase | Sigma G6008 | 7.3 | 25° C. |
| β-glucuronidase | Sigma G0258 | 3.8 | 37° C. |
| Chondroitinase | Sigma C3509 | 7.3 | 37° C. |
| α-mannosidase | Sigma M7257 | 4.5 | 25° C. |
| Hyaluronidase | Sigma H3884 | 5.3 | 37° C. |
| Sulfatase | Sigma S9754 | 5.0 | 37° C. |
| α-glucosidase | Boehringer | 6.0 | 25° C. |

| Enzyme | Catalogue # | pH | Temperature |
| --- | --- | --- | --- |
| | Mannheim | | |

EXAMPLE 18

Protease

The algal solution was warmed to 37° C. in a water bath and the pH adjusted to 7.5 with 0.1N NaOH. Protease was stirred into the solution and reacted for 2 hours at 37° C. The solution was dialyzed against 1 l of distilled water at 4° C. and lyophilized. An increase of activity over the control solution (Table 7, Samples 374-18 D, E, F) was observed after treatment with protease (Tables 7 and 8, Sample 374-18 M and N). The high activity was observed consistently in all protease treated extracts (Table 13 374-55 F and G; Table 15 57 B; Table 16 57 F, Table 17 76 B). Protease treated Sample 374-57 B showed no protein bands on polyacrylamide gel electrophoresis stained with Coomassie Blue as compared with crude extracts showing numerous dark bands.

EXAMPLE 19

Chymotrypsin

The algal solution was placed at 26° C. and the pH of the solution adjusted to pH 7.8 with 0.1N NaOH. The enzyme was stirred into the solution and reacted for 2 hours at 26° C. The reacted solution was dialyzed against 1 liter of water at 4° C. and lyophilized. No decrease of in vitro activity was observed after treatment with chymotrypsin (Table 9, Samples 374-36 L).

EXAMPLE 20

β-xylosidase

The algal solution was placed in a 26° C. chamber and the solution adjusted to pH 5 with 0.1N HCl. The enzyme was stirred into the solution and reacted for 2 hours at 26° C. The reacted solution was dialyzed against 1 liter of water at 4° C. and lyophilized. No decrease of in vitro activity was observed after treatment with xylosidase (Table 9, Samples 374-36 N).

EXAMPLE 21

α-glucosidase 25 mg of dry compound from Example 9 was dissolved in 25 ml water. The solution was adjusted to pH 6 with 0.1N HCl. One milligram of the enzyme was stirred into the algal solution and allowed to react for 4 hours in a 26° C. incubator. The solution was then placed in a Spectrapor 6 tube and dialyzed against 4 l water. The lyophilized powder yielded 22 mg showing no increase or decrease of activity over the control (Table 17, Sample 374-76 G).

EXAMPLE 22

β-n-acetylglucosaminidase

The algal solution was placed in a 26° C. incubator and the solution adjusted to pH 4 with 0.1N HCl. The enzyme was stirred into the solution and reacted 2 hours at 26° C. The reacted solution was dialyzed against 1 liter of water at 4° C. and lyophilized. No decrease of in vitro activity was observed after treatment with the enzyme (Table 9, Samples 374-36 P).

EXAMPLE 23

β-glucosidase 27 mg of lyophilized compound from Example 9 was dissolved in 27 ml of water. The algal solution was placed in a 37° C. bath and the solution adjusted to pH 5 with 0.1N HCl. 1 mg of the enzyme was stirred into the solution and reacted for 4 hours at 37° C. The reacted solution was placed in Spectrapor 6 tubing and dialyzed against 4 liters of water at 4° C. and lyophilized yielding 27 mg. A decrease in activity in vitro was observed after treatment with β-glucosidase (Sample 374-76 D, Table 17).

EXAMPLE 24

β-galactosidase

The algal solution was placed in a 25° C. chamber and the pH of the solution adjusted to 7.3 with 0.1N NaOH. The enzyme was stirred into the solution and reacted for 2 hours at 26° C. The reacted solution was dialyzed against 1 liter of water at 4° C. and lyophilized. A decrease of in vitro activity was observed after treatment with β-galactosidase (Table 1, Samples 432-87 D and E; Table 9, Samples 374-37 A and B).

EXAMPLE 25

β-glucuronidase

The algal solution was placed in a 37° C. bath and the pH of the solution adjusted to 3.8 with 0.1N HCl. The enzyme was stirred into the solution and reacted for 2 hours at 37° C. The reacted solution was dialyzed against 1 liter of water at 4° C. and lyophilized. No significant decrease of in vitro activity was observed after treatment with β-glucuronidase (Table 9, Samples 374-36 Q and R).

EXAMPLE 26

Chondroitinase

The algal solution was placed in a 37° C. water bath and the pH of the solution adjusted to 7.3 with 0.1N NaOH. The enzyme was stirred into the solution and reacted to 2 hours at 37° C. The reacted solution was dialyzed against 1 liter of water at 4° C. and lyophilized. No decrease of activity was observed after treatment with chondroitinase (Table 11, Samples 374-39 Y and Z).

EXAMPLE 27

α-mannosidase

The algal solution was placed in a 26° C. incubator and the pH of the solution adjusted to 4.5 with 0.1N HCl. The enzyme was stirred into the solution and reacted for 2 hours at 26° C. The reacted solution was dialyzed against 1 liter of water at 4° C. and lyophilized. No decrease of activity was observed after treatment with mannosidase (Table 7, Samples 374-18 G, H, I; and Table 8, Sample 374-34 B).

EXAMPLE 28

Hyaluronidase

The algal solution was placed in a 37° C. water bath and the pH of the solution adjusted to 5.3 with 0.1N HCl. The enzyme was stirred into the solution and reacted for 2 hours at 37° C. The reacted solution was dialyzed against 1 liter of water at 4° C. and lyophilized. No significant decrease or increase of in vitro activity was observed after treatment with hyaluronidase (Table 11, Samples 374-40 G to L and Table 17, 374-76 E).

EXAMPLE 29

Sulfatase 25 mg of compound from Example 9 was dissolved in 25 ml water. The algal solution was warmed in a 37° C. water bath and the solution adjusted to pH 5.0 with 0.1N HCl. 1 mg of the enzyme was stirred into the solution and reacted for 4 hours at 37° C. The solution was then dialyzed against water at 4° C. and lyophilized. No decrease in activity was observed after treatment with sulfatase (Table 17, Sample 374-76 F).

EXAMPLE 30 in vitro assay

Bioassays with herpes simplex virus in vitro and in vivo were undertaken to follow the improvement of activity of the algal extractions.

Culture and assay methods follow those described in Lennette and Schmidt (1979) for herpes simplex virus and Vero cells with minor modifications. A detailed description of methods used follows.

Herpesvirus Strains

Shealey strain of herpes simplex type 1 (HSV-1) and Curtis (penile plaque) strain of herpes simplex type 2 (HSV-2) were low passage isolates obtained from Jang. O. Oh, M.D. (1972), Proctor Foundation, University of California at San Francisco. One milliliter aliquots of 100 ml pools of virus were sealed in glass ampules and kept frozen at −70° C. until used.

Cell Cultures

African Green Monkey (*Cercapithicus aethiops*) kidney cells were obtained from The American Type Culture Collection (Hatt, 1979) Vero ATCC CCl 81, as their 121st serial subcultures from tissue of origin.

Culture Media

Cells and viruses are maintained on media with the following formulations and with components purchased from MA Bioproducts, 11841 Mississippi Avenue, Los Angeles, Calif. 90025. Media components are added sequentially under sterile conditions with swirling to thoroughly mix nutrients.

GROWTH MEDIA

Used for maintaining cell stocks and planting tubes.

375 mls de-ionized sterile $H_2O$ 50 mls Eagles MEM 10× concentration 50 mls Fetal Calf Serum Gibco #200-640 (inactivated 56° C.×1 hour)

5.0 mls Penicillin-Streptomycin (5,000 u/ml Pen-5,000 mcg/ml Strep)

5.0 mls Anti-PPLO 100× concentrate 6.0 mls L-glutamine 200 mM 0.1 mls Gentamycin 10 ug/ml 15 mls 7.5% Bicarb to yield pH 7.8–8.0

MAINTENANCE MEDIA (MM)

Used for re-feeding specimens.

To the above recipe decrease the amount of Fetal Calf Serum to 11 mls and use 450 mls sterile $H_2O$ in place of 375 mls.

PANCREATIN-VERSENE TRYPSIN (PVT)

50 mls Trypsin-EDTA 10×
100 mls Pancreatin 2.5% (10×)
330 mls Phosphate Buffered Saline (PBS) without Mg and Ca salts
0.5 mls Phenol Red 0.5%
10–20 mls 7.5% Bicarbonate

BICARBONATE 7.5%

37.5 g Powdered Sodium Bicarbonate
500 mls Sterile deionized $H_2O$

HANK'S (or EARL'S) BSS w/Ca and Mg

Use when changing media.
50 mls Hank's 10× w/Ca and Mg
450 mls Sterile deionized $H_2O$
6 mls Pen-Strep (5,000 u/ml Pen-5,000 mcg/ml Strep)
15 mls 7.5% Bicarbonate

HANK'S BSS WITHOUT Ca and Mg

Used for washing cell stock bottles, rinsing monolayer cultures before inoculation, and neutralizing acidic waste products produced during growth.
50 mls Hank's 10× w/o Ca and Mg
450 mls Sterile deionized $H_2O$
0.5 mls Phenol Red 0.5%
15 mls 7.5% Bicarbonate

Vero Cell Culture

Vero cell stock cultures are grown and maintained in graduated 16 oz. Brockway Glass Co. reaction/culture bottles with one flat side. Cells are released from the flat wall of the bottle by gentle enzyme digestion and are propagated into new stock cultures and assay vessels using the following methods. Stock cultures are incubated at 37° C. in a humidified atmosphere of 5 percent carbon dioxide in air.

Vero Stock Culture

Cells are planted every Friday morning for tube plants needed for the following week and for re-stocking cells into bottles. PVT is then thawed and HBSS and Growth Media are warmed in a 37° C. water bath. Using an inverted compound microscope, 16 oz. culture bottles are checked for healthy confluent cell monolayers. This usually occurs in 7 days. Growth media is decanted from the bottle. Cultures are washed with 25 mls HBSS without Ca and Mg and decanted. The cell surface is rinsed with 7.0 mls PVT and decanted. 2.5 mls of PVT are added and bottles placed in a 37° C. incubator. Bottles are checked in 5 min. for cells coming off of the glass surface and then shaken gently to assist this process. After approximately 15 minutes, when the entire cell sheet is detached from the surface, bottles are removed from the incubator. 12.5 mls Growth Media is added to each bottle and the cuture is shaken well. The contents of all bottles are transferred into a sterile 100 ml bottle.

For cell counts, the 100 ml bottle containing the cell suspension is shaking vigorously and an aliquot of cell suspension using a plugged sterile pasteur pipet is drawn up. Both sides of a cleaned hemocytometer are charged with drops of the suspension. The 4 large squares in each corner per side are counted as for white blood cell counts. The average of the 2 sides is computed and divided 4 multiplied 10, then multiplied by 1000 to arrive at the number of cells/ml.

Each sterile glass 16 oz. stock culture bottle is reinoculated with $3 \times 10^6$ cells and 70 mls growth media is added. They are mixed gently and placed in a 37° C. incubator with a humidified atmosphere of 5 percent carbon dioxide in air. An aliquot of cells is placed in a 100 ml sterile glass bottle and diluted in growth media to contain 250,000 cells/ml. The cell solution is placed on a mixer with a magnetic spin bar stirring slowly. Sterile 150×16 mm tubes are placed in slant racks. Using a 10 ml pipet, 1 ml of cell suspension is delivered to each tube. A #1 silicone rubber stopper is inserted on each tube tightly. Each tube is marked to show side of cell growth. Tubes are gently shaken and incubated at 37° C. Thio tubes are inoculated with 1 ml of cell suspension for sterility test. Each Monday morning stock bottles are examined for healthy cells, tubes for confluent, healthy monolayer and thio tubes for sterility.

Virus Infectivity

Tissue culture infectious dose 50 ($TCID_{50}$) was determined as described by Lennette and Schmidt (1979). Virus infectivity was titrated on confluent Vero cell monolayers in 150×16 mm tubes and cytopathic effect estimated by direct examination at 40× magnification using a Leitz Wetzlar compound microscope with P1 4×, P1 10×, pV 25×, P1 40×, Apo Oil 100× objectives and Periplan 10× oculars. Plaques are produced 2–3 days after infection with appropriate concentrations of HSV-1 and maximum production of plaques occurs within 5 days. Calculations of 50% infection endpoints were based on formulae of Reed and Muench (1937). After 3 days of infection with HSV-1 the preparation showed a $10^{3.33}$ $LD_{50}$ of $TCID_{50}$ and at 5 days it showed a $10^{5.50}$ $LD_{50}$ of $TCID_{50}$. Serial dilutions of algal samples were generally titrated against a $10^{-3}$ (1000 fold) dilution of the HSV-1 which approximated the $TCID_{50}$ at 3 days and 100 $TCID_{50}$ at five days.

Antiviral Agents

Dried compounds were weighed at 1 to 5 milligrams and placed in sterile Falcon 2059 17×11 mm polypropylene tubes with caps. Weighed samples were transported in a chilled styrofoam 20×20×15 cm ice chest for 45 minutes to the assay laboratory. Maintenance Medium (MM) was added to samples bringing the concentration to 1.0 mg/ml, 20 mg/ml, or 100 mg/ml. The solutions were mixed for 1–5 minutes on a VWR K55G vortex mixer at maximum speed setting. The solutions were allowed to stand 12–24 hours at 4° C. and vortex mixed again to insure dissolution of the algal samples into the maintenance medium. Ten fold dilutions were made by adding 0.1 ml of the algal concentrate to 0.9 ml fresh MM. Serial dilutions to concentrations of $1 \times 10^{-4}$ mg/ml were made in this manner. New sterile Falcon 7522 graduated 1 ml serological pipets were used for each volume measurement to prevent pipet error. From the final $1 \times 10^{-4}$ mg/ml solution, 0.1 ml was removed and discarded so that each of the serial dilutions had a 0.9 ml total volume.

To test for viral aggregative activity of the compound, the lowest active (0 CPE) concentration of algal extract was prepared with various concentrations of virus. Each solution was filtered through Millipore Millex-GS 0.22 um filter units with 3 or 5 cc Stylex disposible syringes. Controls were unfiltered virus/antiviral solutions and the same virus dilutions filtered and unfiltered. 0.4 ml of each sample was inoculated on confluent monolayer Vero cells for 2 hours.

in vitro Susceptibility of Viruses

Confluent cell monolayers were treated either with (1) constant concentration of virus and varying concentrations of antiviral compound that were mixed together 30 minutes prior to application to cells; (2) with antiviral compound 2 hours after viral infection; or (3) with varying concentrations of virus and constant concentrations of antiviral compound.

(1) Five milliliters of $10^{-2}$ HSV-1 (100 fold dilution of stock herpes simplex virus) were made by 10 fold serial dilutions of stock HSV-1. 0.1 ml of $10^{-2}$ HSV-1 was added to 0.9 ml of various cocentrations of antiviral compound extract resulting in a $10^{-3}$ dilution of HSV-1. Growth medium was poured off from Vero cultures. Cell cultures were rinsed with 1 ml Hank's BSS without Ca and Mg and the rinse poured off and discarded. 0.4 ml of the antiviral compound and virus solution was transferred to the cell culture and swirled in the tube to coat the monolayer. The tube culture was replaced into its slant rack with the cell layer on the bottom side in a 37° C. incubator for 2 hours. After the 2 hour infection period, the culture was removed from the incubator and the inoculum was replaced with 1 ml fresh 37° C. MM. The culture was corked and set on the slant in a 37° C. incubator until scored for HSV-1 plaque. As controls, cultures with $10^{-3}$ HSV-1 and cultures with no virus, but with media changes were made and treated as the above cultures.

(2) 0.4 ml of $10^{-3}$ HSV-1 (1000× dilution of stock herpes simplex virus) was added to confluent monolayer Vero cultures in 150×16 mm tubes that had previously been rinsed with 1 ml each of 37° C. Hank's BSS without Ca or Mg. The virus inoculum was allowed to infect for 2 hours, after which the tube cultures were rinsed gently three times with 3 mls of 37° C. Hank's BSS without Mg or Ca. The final rinse was poured off and 1 ml of antiviral compound was added to the culture and allowed to react for 1-24 hours at 37° C. At the end of the treatment period, the algal extract was poured off followed by 5-5 ml rinses with Hank's BSS without Mg and Ca. Finally, 1 ml of MM was added to each culture and the cultures were sealed, slanted and placed in 37° C. until read.

(3) Ten fold serial dilutions of HSV-1 stock were made by adding 0.5 ml of virus concentrate to 4.5 ml of MM. The solution was shaken and the process repeated such that $10^{-1}$ and $10^{-2}$ serial dilutions were obtained. To 0.9 ml aliquots of constant concentration of antiviral compounds, 0.1 ml of stock HSV-1 and $10^{-1}$ and $10^{-2}$ dilutions were added and mixed. The solution was allowed to react for 30 minutes at room temperature. The solution was shaken briefly and 0.4 ml withdrawn and added to monolayer cultures that had been rinsed and decanted of medium. The infection was run for 2 hours after which the inoculum was poured off and replaced with maintenance medium. The culture was replaced in a 37° C. incubator until read.

Scoring of Cultures

Infected cultures were read on the third day of inoculation for plaque counts and on the fifth day for total cytopathic effect. Separate holes in the monolayer or groups of giant cells were counted as plaques. Plaques were counted from live cultures using a Leitz Wetzlar compound microscope.

Total cytopathic effect (CPE) was estimated based on plaque count or loss of monolayer read at 40× magnification. Compounds assayed against HSV-1 in vitro were considered active to the level of zero plaque formation or zero CPE.

EXAMPLE 31 in vivo Assay

Bioassays were undertaken at Lilly Research Laboratories, Indianapolis by Dr. John Lavender using the Guinea Pig cutaneous model for HSV-1 and the Guinea Pig intravaginal model for HSV-2 for confirmation of our previously observed results. Assay methods were transmitted by Dr. Lavender.

Model for Intravaginal Herpes Simplex Type II (HSV-2) in Guinea Pigs

In this model, female Hartley albino guinea pigs at 275 to 325 grams were first swabbed intravaginally with physiological saline to remove potential virus inhibitors. The Rapp strain of HSV-2 lot 2-1-24-80 was used. The virus was then inoculated intravaginally with an absorbent cotton swab containing approximately $2\times10^4$ PFU. Treatment was initiated about 3 hours after infection on day 1 by intravaginal inoculation by syringe of the drug in an appropriate vehicle. Each guinea pig was treated twice daily on day 1 through day 5 for a total of 10 treatments. Positive and negative control animals were included in each drug group. Five or more animals are used in each drug and control groups. The positive controls were treated with 1.0 phosphonoacetic acid in the same vehicle as the drug. The negative controls were treated with the drug vehicle only. Starting on day 5 each animal was scored by 2 persons using 0 to 4+ for each of four symptoms: inflammation, discharge, vesiculation, and necrosis. Scoring was continued on days 7, 8 and 9. A top score of 16 is possible for each guinea pig group. The daily scores are averaged for each group of guinea pigs, and from this data a final mean score was calculated.

Model for Cutaneous Herpes Simplex Type 1 (HSV-1) on Guinea Pigs

The hair was shaven from the back of each female Hartley Albino guinea pig, and a large smooth skin area was produced by additional treatment with a depilatory. Guinea pigs weighed 275 to 325 grams each. Four areas of the epilated guinea pig back were then inoculated cutaneously with HSV-1 using a Sterneedle triggered ten times in each area. The Stone strain of HSV-1 lot number 1-5-1-81 was used. The inoculum placed on each skin area contains approximately $1\times10^5$ PFU of virus which insured the development of consistent rosette herpetic plaque in 96-120 hours on untreated animals.

To test a sample compound, animals were inoculated on the morning of day one and each area was then drug treated twice during the afternoon of day one and thereafter twice daily through day 5 for a total of ten treatments per area. Positive and negative control animals were included in each experiment. The positive control animals were treated with 0.5 to 1.0 percent phosphonoacetic acid (PFA) suspended in the same vehicle as the test drug. The negative control animals were treated with the drug vehicle only. Four or more animals were used for each drug and control group. Plaque for each area were scored 0 to 4+ beginning on day 5. On day 7 the hair was again epilated and plaque scoring was continued daily through day 9. Two persons scored each animal each day. From this data the average daily score was calculated for the number of treated and control areas. The daily average scores were then used to give the final mean score for each drug and control group. Using this system, the highest final mean score per group was 4+.

RESULTS in vitro Assay

Results of in vitro assays are given in Tables 1 through 20. A comparison of the inhibitory activities of major algal preparations is given in Table 32. Sample numbers are given in dated sequence, corresponding to the notebook identification followed by a hyphen and notebook page number (e.g. 374-64). The letter following the page number designates the specific assay.

Water extracts assayed on a dilution gradient against herpes simplex virus Type 1 (HSV-1) were active at approximately 1 mg/ml concentration (Table 19, Samples 462-10A and 462-18A). Post infection treatments with water extracts showed inhibition of the virus from 0.1 to 1.0 mg/ml concentrations (Table 20, Samples 462-10A through 462-28C).

Crude buffered extracts assayed on a dilution gradient showed consistent activity (O CPE) to 1 mg/ml concentration in most assays against HSV-1 (Samples 432-97 A, C, G, K; 374-4 A-C). Treatment of cultures with the crude buffered extract two hours after inoculation with the virus showed low inhibitory activity at 1 mg/ml (Table 1, Sample 432-86L). Algae extracted in high salt (2.5N NaCl) concentration with no buffer yielded higher activity to 0.1 mg/ml (374-5 A to C; 34 J). Post-infection treatment with this extract showed activity (Table 8, Samples 374-34I) that was better than the buffered extracts.

Algae homogenized by pulverization in liquid nitrogen and extracted a second time in the presence of Triton X-100 showed activity to 0.01 mg/ml (assays 432-87 A-C; 89 A-E).

Acetone precipitates of the crude extracts were very difficult to dissolve into the assay medium. Results of assays are, therefore, inconsistent regarding the lowest concentration required for inhibition of the virus. Activities ranged from 0.01 mg/ml (assays 374-17 D, E, F) to 0.1 mg/ml (assays 374-18 D, E, F).

Ethanol precipitate fractions of algal extracts in high salt concentration showed high activity. Precipitates at 20% EtOH were active to 0.01 mg/ml (374-17 M and N). At 33% EtOH, a precipitate was active to 0.001 mg/ml (374-17 O, P, Q) although activity of this fraction was commonly found at 0.01 mg/ml (40 O). Precipitates from higher concentrations of EtOH showed no activity (374-17 R-W). Large batches (1-5 liters) of extract precipitated with ethanol at 1:0.5 v/v treatment in 2.5N NaCl showed activity to 0.01 mg/ml (374-18 A, B, C; 374-34 N, O; 374-37 U, V; 374-40 O, P).

Acetone precipitates that were dissolved and precipitated by ethanol 1:2 v/v in high salt concentration also showed 0.1 mg/ml activity (374-52 F, G, H). When titrated against increasing concentrations of virus, this preparation showed complete inhibition to HSV-1 $10^{-1}$ dilution without (374-55 K, L, M) or with filtration (374-55 N, O, P)

Enzyme Treatment

No decrease in activity of algal extracts was noted after reaction with protease (374-18 M), chymotrypsin (374-36 K and L), β-xylosidase (374-36 M and N), β-n-acetylglucosaminidase (374-36 O and P), β-glucuronidase (374-36Q and R), α-glucosidase (374-76 G), chondroitinase (374-39 X and Y), α-mannosidase (374-18 G, H, I, 374-34 B and 374-76C), or sulfatase (374-76 F).

Activity decreased significantly after treatment of extracts with β-glucosidase (374-76D). Activity also decreased after treatment with β-galactosidase (432-87 D, E and 374-37 A, B). Minor decreases in activity were observed in extracts digested with hyaluronidase (374-40 G-L and 374-76 E). Activity increased after treatment with proteases (374-18 M and N; 55 F and G; 57 B; 57 F; 76 B).

Control Sulfated Polysaccharides

Polysaccharides tested against HSV-1 for comparison showed lower activity than the algal extract. Assayed were carrageenan (432-87 F, G), agar (374-42 I-K) and chondroitin (374-42 L-N).

Periodic Acid

Algal extracts oxidized with periodic acid showed no significant change in activity (374-37 E to H).

Characterization

1. Molecular Weight

Activity in crude extracts was retained by 50,000 and 10,000 MW membrane filters (374-11 K to N). Most of the activity in EtOH precipitates was retained by membrane filters with 100,000 Dalton or lower porosities for globular protein (374-37 I to N). Active components of extracts treated with strong acid passed through 50,000 MW membranes (374-37 O to T).

2. Acid and Base Treatment

At room temperature, treatment with 1N NaOH decreases activity (374-35 E). 1N HCl (374-35 E) does not change the in vitro activity. All activity is lost completely with acid treatment at 100° C. for 4 hours or more (374-39 A to X). The precipitate from this hot acid treatment remained active (374-40 A-D).

3. Heating

Algal extracts in aqueous solutions showed no loss of activity when heated up to 60° C. (374-17 J, K, L; also see 374-4 F to K for 25° C., 37° C., and 50° C.).

4. Elemental Analyses

Elemental analyses by Galbraith Laboratories (Knoxville, Tenn.) gave the contents listed in Table 31 for water extracts.

Cation Exchange Chromatography

Stepwise salinity fractionation on mini-columns (374-6 and 7) showed retention of active components at pH 5 (374-6 J-L) and complete elution at pH 6 (374-7 A-C).

Solvent Extracts

Solvent extracts showed in vitro activity. Acetone extracts (Table 18, Samples 462-63 and 374-95) required higher concentration for inhibition of the virus than chloroform extracts (Table 18, Samples 462-66).

In Vivo Assay

Crude and treated extracts of *Cryptosiphonia woodii* showed significant inhibition of activity in the guinea pig vaginitis model when applied three hours after infection with HSV-2. Results of the intravaginal assay are given in Tables 21, 22, 24 and 27 through 30. The crude buffered extract (Table 29, Sample EP 1032), Triton X-100 and protease treated algal extract (Table 22, Samples EP 1008 and EP 1019), and non-buffered ethanol precipitate (Table 21, Sample EP 1013) all showed antiviral activity in this model. Algal extracts purified for polysaccharides by lipid removal with solvents (Table 27, Samples EP 1025 through 1028) followed by protein denaturation (Table 27, Samples EP 1025, EP 1027, EP 1028; and Table 28, EP 1029) and/or selective precipitation (Table 25, Sample EP 1023; and Table 27, Sample EP 1026) showed no activity in the guinea pig vaginitis model.

Various samples were applied cutaneously against HSV-1 (Tables 23 and 25) or intraperitoneally against HSV-2 (Table 26), but no activity was observed in these models.

A comparison of activities of major preparations of algal extracts is given in Table 32.

REFERENCES

1. Deig, E. F., D. W. Ehresmann, M. T. Hatch, and D. J. Riedlinger. 1974. Inhibition of herpesvirus replication by marine algae extracts. Antimicrob. Agents Chemother. 6(4): 524–525.

2. Ehresmann, D. W., E. F. Deig, M. T. Hatch, and D. J. Riedlinger. 1975. Characterization of the anti-herpesvirus activity in extracts of marine algae. Annual Meeting (Abstract A-7), American Society for Microbiology, May 2–7, 1975.

3. Hatch, M. T., D. W. Ehresmann, E. F. Deig, and N. A. Vedros. 1977. Further studies on the chemical composition and an initial in vivo evaluation of antiviral material in extracts of macroscopic marine algae. Paper, IXth International Seaweed Symposium, Santa Barbara, Calif. (Abstract 154). J. Phycol. 13, Supplement, June 1977.

4. Deig, E. F., D. J. Riedlinger, D. W. Ehresmann, and M. T. Hatch. 1977. Evaluation of extracts of marine algae for antiviral activity in experimental herpes simplex infections of infant mice. pp. 4-96–4-104. In Naval Biosciences Laboratory 52nd Technical Progress Report, April 1977, University of California, Berkeley.

5. Ehresmann, D. W., E. F. Deig, M. T. Hatch, L. H. DiSalvo, and N. A. Vedros. 1977. Antiviral substances from California marine algae. J. Phycol. 13(1):37–40.

6. Richards, J. T., E. R. Kern, L. A. Glasgow, J. C. Overall Jr., E. F. Deign (sic), and M. T. Hatch. 1978. Antiviral activity of extracts from marine algae. Antimicrob. Agents Chemother. 14(1): 24–30.

7. Deig, E. F., M. T. Hatch, and A. M. Nonomura. 1979. Development of dermal lesions in adult mice infected with *Herpes simplex* virus: Application of the model in the evaluation of antiherpesvirus substances from marine algae. pp. 1-153–1-158. In Naval Biosciences Laboratory 55th Technical Progress Report, March 1979. University of California, Berkeley.

8. Hatch, M. T., D. W. Ehresmann, and E. F. Deig. 1979. Chemical characterization and therapeutic evaluation of anti-herpesvirus polysaccharides from species of Dumontiaceae. pp. 343–363. In (H. A. Hoppe, T. Levring, and Y. Tanaka, eds.) Marine Algae in Pharmaceutical Science. Walter de Gruyter, Berlin, N.Y.

9. Ehresmann, D. W., E. F. Deig, and M. T. Hatch. 1979. Anti-viral properties of algal polysaccharides and related compounds. pp. 293–302. In (H. A. Hoppe, T. Levring, and Y. Tanaka, eds.) Marine Algae in Pharmaceutical Science, Walter de Gruyter, Berlin, N.Y.

10. Pigman, W., D. Horton, J. D. Wander. 1980. *The Carbohydrates Chemistry and Biochemistry*. Academic Press, N.Y. 1627 pp.

11. Oh, Jang O. 1972. Ocular Pathogenicity of Types 1 and 2 *Herpesvirus hominis* in rabbits. Infection and Immunology 5: 412–413.

12. Hatt, H. D. (Ed.). 1979. The American Type Culture Collection. Catalogue of Strains II. 2nd Ed. 12301 Parklawn Drive, Rockville, MD. 20852. p.54

13. Lennette, E. H. and N. J. Schmidt. 1979. *Diagnostic Procedures for: Viral, Rickettsial and Chlamydial Infections*, 5th ed. American Public Health Assoc., Inc. Washington, D.C. 1138 pp.

14. Reed, L. J. Muench, H.: A simple method of estimating fifty percent endpoints. Amer. J. Hyg. 27, 493–497 (1938).

15. Abott, I. A. and Hollenberg, G. J. 1976. *Marine Algae of California*, Stanford University Press, p. 361

TABLE 1

| Sample Number | Species | Extract purification | mg/ml Concentrate | Infection Start data | Reading 1 Date | Percent CPE | Reading 2 Date | Percent CPE |
|---|---|---|---|---|---|---|---|---|
| 432-67A | C. woodii | EtOH ppt. | 10.0 | 11 July 1981 | 14 July 1981 | 0 | 14 July 1981 | 0 |
| 432-67B | C. woodii | EtOH ppt. | 1.0 | 11 July 1981 | 14 July 1981 | 0 | 14 July 1981 | 0 |
| 432-67C | C. woodii | EtOH ppt. | 0.1 | 11 July 1981 | 14 July 1981 | 30 | 14 July 1981 | 20 |
| 432-67D | C. woodii | EtOH ppt. | 0.01 | 11 July 1981 | 14 July 1981 | 75 | 14 July 1981 | 75 |
| 432-67E | C. woodii | EtOH ppt. | 0.001 | 11 July 1981 | 14 July 1981 | 75 | 14 July 1981 | 75 |
| | HSV-1 | Control | $10^{-3}$ | 11 July 1981 | 14 July 1981 | 75 | 14 July 1981 | 75 |
| | Buffer | Control | | 11 July 1981 | 14 July 1981 | 0 | 14 July 1981 | 0 |
| 432-83A | C. woodii | Crude | 1.0 | 29 July 1981 | 2 Aug. 1981 | 0 | 2 Aug. 1981 | 0 |
| 432-83B | C. woodii | Crude | 0.10 | 29 July 1981 | 2 Aug. 1981 | 0 | 2 Aug. 1981 | 0 |
| | HSV-1 | Control | $10^{-3}$ | 29 July 1981 | 2 Aug. 1981 | 90 | 2 Aug. 1981 | 100 |
| | Buffer | Control | | 29 July 1981 | 2 Aug. 1981 | 0 | 2 Aug. 1981 | 0 |
| 432-86L | C. woodii | Crude/infect:post-treat | 1.0 | 5 Aug. 1981 | 8 Aug. 1981 | 20 | 8 Aug. 1981 | 15 |
| 432-87A | C. woodii | Crude Triton | 1.0 | 5 Aug. 1981 | 8 Aug. 1981 | 0 | 8 Aug. 1981 | 0 |
| 432-87B | C. woodii | Crude Triton | 0.1 | 5 Aug. 1981 | 8 Aug. 1981 | 0 | 8 Aug. 1981 | 0 |
| 432-87C | C. woodii | Crude Triton | 0.01 | 5 Aug. 1981 | 8 Aug. 1981 | 0 | 8 Aug. 1981 | 0 |
| 432-87D | C. woodii | Crude w/galactosidase | 1.0 | 5 Aug. 1981 | 8 Aug. 1981 | 0 | 8 Aug. 1981 | 0 |
| 432-87E | C. woodii | Crude w/galactosidase | 0.1 | 5 Aug. 1981 | 8 Aug. 1981 | 20 | 8 Aug. 1981 | 15 |
| 432-87F | Eucheuma | Sigma Carrageenan | 1.0 | 5 Aug. 1981 | 8 Aug. 1981 | 0 | 8 Aug. 1981 | 0 |
| 432-87G | Eucheuma | Sigma Carrageenan | 0.1 | 5 Aug. 1981 | 8 Aug. 1981 | 10 | 8 Aug. 1981 | 10 |
| | HSV-1 | Control | $10^{-3}$ | 5 Aug. 1981 | 8 Aug. 1981 | 70 | 8 Aug. 1981 | 70 |
| | Buffer | Control | | 5 Aug. 1981 | 8 Aug. 1981 | 0 | 8 Aug. 1981 | 0 |

TABLE 2

| Sample Number | Species | Extract purification | mg/ml Concentrate | Infection Start data | Reading 1 Date | Percent CPE | Reading 2 Date | Percent CPE |
|---|---|---|---|---|---|---|---|---|
| 432-89A | C. woodii | Crude Triton X-100 | 1.0 | 21 Aug. 1981 | 24 Aug. 1981 | 0 | 24 Aug. 1981 | 0 |
| 432-89B | C. woodii | Crude Triton X-100 | 0.1 | 21 Aug. 1981 | 24 Aug. 1981 | 0 | 24 Aug. 1981 | 0 |
| 432-89C | C. woodii | Crude Triton X-100 | 0.01 | 21 Aug. 1981 | 24 Aug. 1981 | 0 | 24 Aug. 1981 | 0 |
| 432-89D | C. woodii | Crude Triton X-100 | 0.001 | 21 Aug. 1981 | 24 Aug. 1981 | 15 | 24 Aug. 1981 | 10 |
| 432-89E | C. woodii | Crude Triton X-100 | 0.0001 | 21 Aug. 1981 | 24 Aug. 1981 | 10 | 24 Aug. 1981 | 10 |
| 432-89F | C. woodii | Crude Triton, post inf | 0.1 | 21 Aug. 1981 | 24 Aug. 1981 | 30 | 24 Aug. 1981 | 30 |
|  | HSV-1 | Control | $10^{-3}$ | 21 Aug. 1981 | 24 Aug. 1981 | 30 | 24 Aug. 1981 | 30 |
| 432-97A | C. woodii | Crude 1st extract | 1 | 2 Nov. 1981 | 6 Nov. 1981 | 5 | 6 Nov. 1981 | 5 |
| 432-97B | C. woodii | Crude 1st extract | 0.1 | 2 Nov. 1981 | 6 Nov. 1981 | 100 | 6 Nov. 1981 | 100 |
| 432-97C | C. woodii | Crude 2nd extract | 1 | 2 Nov. 1981 | 6 Nov. 1981 | 0 | 6 Nov. 1981 | 0 |
| 432-97D | C. woodii | Crude 2nd extract | 0.1 | 2 Nov. 1981 | 6 Nov. 1981 | 5 | 6 Nov. 1981 | 0 |
| 432-97E | C. woodii | Crude dialysate | 1 | 2 Nov. 1981 | 6 Nov. 1981 | 100 | 6 Nov. 1981 | 100 |
| 432-97F | C. woodii | Crude dialysate | 0.1 | 2 Nov. 1981 | 6 Nov. 1981 | 100 | 6 Nov. 1981 | 100 |
| 432-97G | C. woodii | Crude 1st extract | 1 | 2 Nov. 1981 | 6 Nov. 1981 | 0 | 6 Nov. 1981 | 0 |
| 432-97H | C. woodii | Crude 1st extract | 0.1 | 2 Nov. 1981 | 6 Nov. 1981 | 5 | 6 Nov. 1981 | 10 |
| 432-97I | C. woodii | Crude 1st extract | 0.01 | 2 Nov. 1981 | 6 Nov. 1981 | 90 | 6 Nov. 1981 | 90 |
| 432-97J | C. woodii | Crude 1st extract | 0.001 | 2 Nov. 1981 | 6 Nov. 1981 | 100 | 6 Nov. 1981 | 100 |
| 432-97K | C. woodii | Crude 2nd extract | 1.0 | 2 Nov. 1981 | 6 Nov. 1981 | 0 | 6 Nov. 1981 | 0 |
| 432-97L | C. woodii | Crude 2nd extract | 0.1 | 2 Nov. 1981 | 6 Nov. 1981 | 40 | 6 Nov. 1981 | 40 |
| 432-97M | C. woodii | Crude 2nd extract | 0.01 | 2 Nov. 1981 | 6 Nov. 1981 | 100 | 6 Nov. 1981 | 100 |
| 432-97N | C. woodii | Crude 2nd extract | 0.001 | 2 Nov. 1981 | 6 Nov. 1981 | 100 | 6 Nov. 1981 | 100 |
|  | HSV-1 | Control | $10^{-3}$ | 2 Nov. 1981 | 6 Nov. 1981 | 100 | 6 Nov. 1981 | 100 |

TABLE 3

| Sample Number | Species | Extract purification | mg/ml Concentrate | Infection Start date | Reading 1 Date | Percent CPE | Reading 2 Date | Percent CPE |
|---|---|---|---|---|---|---|---|---|
| 374-4A | C. woodii | Crude | 1.0 | 12 Nov. 1981 | 16 Nov. 1981 | 0 |  |  |
| 374-4B | C. woodii | Crude | 1.0 | 12 Nov. 1981 | 16 Nov. 1981 | 0 |  |  |
| 374-4C | C. woodii | Crude | 1.0 | 12 Nov. 1981 | 16 Nov. 1981 | 0 |  |  |
| 374-4D | C. woodii | Crude pH 8 | 1.0 | 12 Nov. 1981 | 16 Nov. 1981 | 0 |  |  |
| 374-4E | C. woodii | Crude pH 8 | 1.0 | 12 Nov. 1981 | 16 Nov. 1981 | 0 |  |  |
| 374-4F | C. woodii | Crude 25° C. | 1.0 | 12 Nov. 1981 | 16 Nov. 1981 | 0 |  |  |
| 374-4G | C. woodii | Crude 25° C. | 1.0 | 12 Nov. 1981 | 16 Nov. 1981 | 0 |  |  |
| 374-4H | C. woodii | Crude 37° C. | 1.0 | 12 Nov. 1981 | 16 Nov. 1981 | 0 |  |  |
| 374-4I | C. woodii | Crude 37° C. | 1.0 | 12 Nov. 1981 | 16 Nov. 1981 | 0 |  |  |
| 374-4J | C. woodii | Crude 50° C. | 1.0 | 12 Nov. 1981 | 16 Nov. 1981 | 0 |  |  |
| 374-4K | C. woodii | Crude 50° C. | 1.0 | 12 Nov. 1981 | 16 Nov. 1981 | 0 |  |  |
| 374-5A | C. woodii | Crude salt | 1.0 | 12 Nov. 1981 | 16 Nov. 1981 | 0 |  |  |
| 374-5B | C. woodii | Crude salt | 0.1 | 12 Nov. 1981 | 16 Nov. 1981 | 0 |  |  |
| 374-5C | C. woodii | Crude salt | 0.01 | 12 Nov. 1981 | 16 Nov. 1981 | 45 |  |  |
| 374-5D | C. woodii | Crude | 0.001 | 12 Nov. 1981 | 16 Nov. 1981 | 100 |  |  |
|  | HSV-1 | Control | $10^{-3}$ | 12 Nov. 1981 | 16 Nov. 1981 | 100 |  |  |
|  | HSV-1 | Control | $10^{-3}$ | 12 Nov. 1981 | 16 Nov. 1981 | 100 |  |  |
| 374-6 | C. woodii | Cation exchange |  |  |  |  |  |  |
| 374-6A | C. woodii | pH4/10 mM NaCl | 1.0 | 20 Nov. 1981 | 23 Nov. 1981 | 0 | 25 Nov. 1981 | 0 |
| 374-6B | C. woodii | pH4/10 mM NaCl | 0.1 | 20 Nov. 1981 | 23 Nov. 1981 | 0 | 25 Nov. 1981 | 0 |
| 374-6C | C. woodii | pH4/50 mM NaCl | na | 20 Nov. 1981 | 23 Nov. 1981 | 0 | 25 Nov. 1981 | 5 |
| 374-6D | C. woodii | pH4/100 mM NaCl | na | 20 Nov. 1981 | 23 Nov. 1981 | 30 | 25 Nov. 1981 | 90 |
| 374-6E | C. woodii | pH4/500 mM NaCl | na | 20 Nov. 1981 | 23 Nov. 1981 | 30 | 25 Nov. 1981 | 90 |
| 374-6F | C. woodii | pH4/1000 mM NaCl | na | 20 Nov. 1981 | 23 Nov. 1981 | 30 | 25 Nov. 1981 | 90 |
| 374-6G | C. woodii | pH5/10 mM NaCl | 1.0 | 20 Nov. 1981 | 23 Nov. 1981 | 0 | 25 Nov. 1981 | 0 |
| 374-6H | C. woodii | pH5/10 mM NaCl | 0.1 | 20 Nov. 1981 | 23 Nov. 1981 | 0 | 25 Nov. 1981 | 0 |
| 374-6I | C. woodii | pH5/50 mM NaCl | na | 20 Nov. 1981 | 23 Nov. 1981 | 0 | 25 Nov. 1981 | 5 |
| 374-6J | C. woodii | pH5/100 mM NaCl | na | 20 Nov. 1981 | 23 Nov. 1981 | 25 | 25 Nov. 1981 | 50 |

TABLE 4

| Sample Number | Species | Extract purification | mg/ml Concentrate | Infection Start date | Reading 1 Date | Percent CPE | Reading 2 Date | Percent CPE |
|---|---|---|---|---|---|---|---|---|
| 374-6K | C. woodii | pH5/500 mM NaCl | na | 20 Nov. 1981 | 23 Nov. 1981 | 15 | 25 Nov. 1981 | 30 |
| 374-6L | C. woodii | pH5/1000 mM NaCl | na | 20 Nov. 1981 | 23 Nov. 1981 | 5 | 25 Nov. 1981 | 5 |
| 374-6M | C. woodii | pH6/10 mM NaCl | 1.0 | 20 Nov. 1981 | 23 Nov. 1981 | 0 | 25 Nov. 1981 | 0 |
| 374-6N | C. woodii | pH6/10 mM NaCl | 0.1 | 20 Nov. 1981 | 23 Nov. 1981 | 0 | 25 Nov. 1981 | 0 |
| 374-6O | C. woodii | pH6/50 mM NaCl | na | 20 Nov. 1981 | 23 Nov. 1981 | 0 | 25 Nov. 1981 | 0 |
| 374-7A | C. woodii | pH6/100 mM NaCl | na | 20 Nov. 1981 | 23 Nov. 1981 |  | 25 Nov. 1981 | 0 |
| 374-7B | C. woodii | pH6/500 mM NaCl | na | 20 Nov. 1981 | 23 Nov. 1981 |  | 25 Nov. 1981 | 0 |
| 374-7C | C. woodii | pH6/1000 mM NaCl | na | 20 Nov. 1981 | 23 Nov. 1981 | 0 | 25 Nov. 1981 | 0 |
| 374-7D | C. woodii | pH7/10 mM NaCl | 1.0 | 20 Nov. 1981 | 23 Nov. 1981 | 0 | 25 Nov. 1981 | 0 |
| 374-7E | C. woodii | pH7/10 mM NaCl | 0.1 | 20 Nov. 1981 | 23 Nov. 1981 | 0 | 25 Nov. 1981 | 0 |
| 374-7F | C. woodii | pH7/50 mM NaCl | na | 20 Nov. 1981 | 23 Nov. 1981 | toxic | 25 Nov. 1981 | 16 |
| 374-7G | C. woodii | pH7/100 mM NaCl | na | 20 Nov. 1981 | 23 Nov. 1981 | toxic | 25 Nov. 1981 | 50 |
| 374-7H | C. woodii | pH7/500 mM NaCl | na | 20 Nov. 1981 | 23 Nov. 1981 | toxic | 25 Nov. 1981 | Toxic |
| 374-7I | C. woodii | pH7/1000 mM NaCl | na | 20 Nov. 1981 | 23 Nov. 1981 | toxic | 25 Nov. 1981 | Toxic |
| 374-7J | C. woodii | pH8/10 mM NaCl | 1.0 | 20 Nov. 1981 | 23 Nov. 1981 | 0 | 25 Nov. 1981 | 0 |
| 374-7K | C. woodii | pH8/50 mM NaCl | na | 20 Nov. 1981 | 23 Nov. 1981 | 20 | 25 Nov. 1981 | 30 |
| 374-7L | C. woodii | pH8/100 mM NaCl | na | 20 Nov. 1981 | 23 Nov. 1981 | 30 | 25 Nov. 1981 | 60 |

TABLE 4-continued

| Sample Number | Species | Extract purification | mg/ml Concentrate | Infection Start date | Reading 1 Date | Percent CPE | Reading 2 Date | Percent CPE |
|---|---|---|---|---|---|---|---|---|
| 374-7M | C. woodii | pH8/500 mM NaCl | na | 20 Nov. 1981 | 23 Nov. 1981 | 15 | 25 Nov. 1981 | 40 |
| 374-7N | C. woodii | pH8/1000 mM NaCl | na | 20 Nov. 1981 | 23 Nov. 1981 | 15 | 25 Nov. 1981 | 40 |
| | HSV-1 | Control | $10^{-3}$ | 20 Nov. 1981 | 23 Nov. 1981 | 100 | 25 Nov. 1981 | 100 |
| 374-8A | C. woodii | CMS pH6/10 mM NaCl | 0.1 | 27 Nov. 1981 | 30 Nov. 1981 | 0 | | |
| 374-8B | C. woodii | CMS pH6/10 mM NaCl | 0.001 | 27 Nov. 1981 | 30 Nov. 1981 | 90 | | |
| 374-8C | C. woodii | CMS pH6/1000 mM NaCl | 0.1 | 27 Nov. 1981 | 30 Nov. 1981 | 100 | | |
| 374-8D | C. woodii | CMS pH6/1000 mM NaCl | 0.01 | 27 Nov. 1981 | 30 Nov. 1981 | 100 | | |
| 374-8E | C. woodii | CMS pH6/1000 mM NaCl | 0.011 | 27 Nov. 1981 | 30 Nov. 1981 | 100 | | |
| 374-8F | C. woodii | CMS pH6/1000 mM NaCl | 0.1 | 27 Nov. 1981 | 30 Nov. 1981 | 100 | | |
| | HSV-1 | Control | $10^{-3}$ | 27 Nov. 1981 | 30 Nov. 1981 | 100 | | |

TABLE 5

| Sample Number | Species | Extract purification | mg/ml Concentrate | Infection Start date | Reading 1 Date | Percent CPE | Reading 2 Date | Percent CPE |
|---|---|---|---|---|---|---|---|---|
| 374-11J | C. woodii | Crude | 0.1 | 13 Dec. 1981 | 16 Dec. 1981 | 0 | | |
| 374-11K | C. woodii | PM 10 Filtrate | na | 13 Dec. 1981 | 16 Dec. 1981 | 100 | | |
| 374-11L | C. woodii | PM 10 Retenate | na | 13 Dec. 1981 | 16 Dec. 1981 | 0 | | |
| 374-11M | C. woodii | XM 50 Filtrate | na | 13 Dec. 1981 | 16 Dec. 1981 | 100 | | |
| 374-11N | C. woodii | XM 10 Retentate | na | 13 Dec. 1981 | 16 Dec. 1981 | 0 | | |
| 374-12A | C. woodii | Sephacryl S-200 | na | 21 Dec. 1981 | 24 Dec. 1981 | 0 | | |
| 374-12B | C. woodii | Sephacryl S-200 | na | 121Dec. 1981 | 24 Dec. 1981 | 80 | | |
| 374-12 | HSV-1 | Control | $10^{-3}$ | 21 Dec. 1981 | 24 Dec. 1981 | 100 | | |

TABLE 6

| Sample Number | Species | Extract purification | mg/ml Concentrate | Infection Start date | Reading 1 Date | Percent CPE | Reading 2 Date | Percent CPE |
|---|---|---|---|---|---|---|---|---|
| 374-17A | C. woodii | Crude | 0.1 | 1 Jan. 1982 | 4 Jan. 1982 | 0 | | |
| 374-17B | C. woodii | Crude | 0.01 | 1 Jan. 1982 | 4 Jan. 1982 | 100 | | |
| 374-17C | C. woodii | Crude | 0.001 | 1 Jan. 1982 | 4 Jan. 1982 | 100 | | |
| 374-17D | C. woodii | Acetone ppt | 0.1 | 1 Jan. 1982 | 4 Jan. 1982 | 0 | | |
| 374-17E | C. woodii | Acetone ppt | 0.01 | 1 Jan. 1982 | 4 Jan. 1982 | 0 | | |
| 374-17F | C. woodii | Acetone ppt | 0.001 | 1 Jan. 1982 | 4 Jan. 1982 | 50 | | |
| 374-17G | C. woodii | Charcoal filter | 0.1 | 1 Jan. 1982 | 4 Jan. 1982 | 100 | | |
| 374-17H | C. woodii | Charcoal filter | 0.01 | 1 Jan. 1982 | 4 Jan. 1982 | 100 | | |
| 374-17I | C. woodii | Charcoal filter | 0.001 | 1 Jan. 1982 | 4 Jan. 1982 | 100 | | |
| 374-17J | C. woodii | 60° C. | 0.1 | 1 Jan. 1982 | 4 Jan. 1982 | 0 | | |
| 374-17K | C. woodii | 60° C. | 0.01 | 1 Jan. 1982 | 4 Jan. 1982 | 100 | | |
| 374-17L | C. woodii | 60° C. | 0.001 | 1 Jan. 1982 | 4 Jan. 1982 | 100 | | |
| 374-17M | C. woodii | 20% EtOH ppt | 0.1 | 1 Jan. 1982 | 4 Jan. 1982 | 0 | | |
| 374-17N | C. woodii | 20% EtOH ppt | 0.01 | 1 Jan. 1982 | 4 Jan. 1982 | 0 | | |
| 374-17O | C. woodii | 33% EtOH ppt | 0.1 | 1 Jan. 1982 | 4 Jan. 1982 | 0 | | |
| 374-17P | C. woodii | 33% EtOH ppt | 0.01 | 1 Jan. 1982 | 4 Jan. 1982 | 0 | | |

TABLE 7

| Sample Number | Species | Extract purification | mg/ml Concentrate | Infection Start date | Reading 1 Date | Percent CPE | Reading 2 Date | Percent CPE |
|---|---|---|---|---|---|---|---|---|
| 374-17Q | C. woodii | 33% EtOH ppt | 0.001 | 1 Jan. 1982 | 4 Jan. 1982 | 0 | | |
| 374-17R | C. woodii | 43% EtOH ppt | 0.1 | 1 Jan. 1982 | 4 Jan. 1982 | 100 | | |
| 374-17S | C. woodii | 43% EtOH | 0.01 | 1 Jan. 1982 | 4 Jan. 1982 | 100 | | |
| 374-17T | C. woodii | 43% EtOH | 0.001 | 1 Jan. 1982 | 4 Jan. 1982 | 100 | | |
| 374-17U | C. woodii | 66.6% EtOH | 0.1 | 1 Jan. 1982 | 4 Jan. 1982 | 70 | | |
| 374-17V | C. woodii | 66.6% EtOH | 0.01 | 1 Jan. 1982 | 4 Jan. 1982 | 100 | | |
| 374-17W | C. woodii | 66.6% EtOH | 0.001 | 1 Jan. 1982 | 4 Jan. 1982 | 100 | | |
| | HSV-1 | Control | $10^{-3}$ | 1 Jan. 1982 | 4 Jan. 1982 | 100 | | |
| 374-18A | C. woodii | EtOH ppt | 0.1 | 9 Jan. 1982 | 11 Jan. 1982 | 0 | | |
| 374-18B | C. woodii | EtOH ppt | 0.01 | 9 Jan. 1982 | 11 Jan. 1982 | 0 | | |
| 374-18C | C. woodii | EtOH ppt | 0.001 | 9 Jan. 1982 | 11 Jan. 1982 | 5 | | |
| 374-18D | C. woodii | Acetone ppt | 0.1 | 9 Jan. 1982 | 11 Jan. 1982 | 20 | | |
| 374-18E | C. woodii | Acetone ppt | 0.01 | 9 Jan. 1982 | 11 Jan. 1982 | 100 | | |
| 374-18F | C. woodii | Acetone ppt | 0.001 | 9 Jan. 1982 | 11 Jan. 1982 | 100 | | |
| 374-18G | C. woodii | Acetone ppt + Mannosidase | 0.1 | 9 Jan. 1982 | 11 Jan. 1982 | 0 | | |
| 374-18H | C. woodii | Acetone ppt + Mannosidase | 0.01 | 9 Jan. 1982 | 11 Jan. 1982 | 80 | | |
| 374-18I | C. woodii | Acetone ppt + Mannosidase | 0.001 | 9 Jan. 1982 | 11 Jan. 1982 | 100 | | |
| 374-18M | C. woodii | Acetone ppt + Protease | 0.1 | 9 Jan. 1982 | 11 Jan. 1982 | 0 | | |

TABLE 8

| Sample Number | Speciess | Extract purification | mg/ml Concentrate | Infection Start date | Reading 1 Date | Percent CPE | Reading 2 Date | Percent CPE |
|---|---|---|---|---|---|---|---|---|
| 374-18N | C. woodii | Acetone ppt + | 0.01 | 9 Jan. 1982 | 11 Jan. 1982 | 5 | | |
| 374-18Q | C. woodii | Crude | 0.1 | 9 Jan. 1982 | 11 Jan. 1982 | 0 | | |
| 374-18R | C. woodii | Crude | 0.01 | 9 Jan. 1982 | 11 Jan. 1982 | 7 | | |
| 374-34A | C. woodii | Mannosidase filtrate | na | 14 Jan. 1982 | 17 Jan. 1982 | 100 | | |
| 374-34B | C. woodii | Mannosidase retentate | na | 14 Jan. 1982 | 17 Jan. 1982 | 0 | | |
| 374-34E | C. woodii | Protease filtrate | na | 14 Jan. 1982 | 17 Jan. 1982 | 60 | | |
| 374-34F | C. woodii | Protease retentate | na | 14 Jan. 1982 | 17 Jan. 1982 | 0 | | |
| 374-34G | C. woodii | DMSO:EtOH ppt | 0.01 | 14 Jan. 1982 | 17 Jan. 1982 | 0 | | |
| 374-34H | C. woodii | Crude salt post-infect | 1.0 | 14 Jan. 1982 | 17 Jan. 1982 | 0 | | |
| 374-34I | C. woodii | Crude salt post-infect | 0.1 | 14 Jan. 1982 | 17 Jan. 1982 | 0 | | |
| 374-34J | C. woodii | Crude salt | 1.0 | 14 Jan. 1982 | 17 Jan. 1982 | 0 | | |
| 374-34K | C. woodii | Crude salt | 0.1 | 14 Jan. 1982 | 17 Jan. 1982 | 0 | | |
| 374-34L | C. woodii | EtOH post-infect | 1.0 | 14 Jan. 1982 | 17 Jan. 1982 | 0 | | |
| 374-34M | C. woodii | EtOH post-infect | 0.1 | 14 Jan. 1982 | 17 Jan. 1982 | 0 | | |
| 374-34N | C. woodii | EtOH | 1.0 | 14 Jan. 1982 | 17 Jan. 1982 | 0 | | |
| 374-34O | C. woodii | EtOH | 0.1 | 14 Jan. 1982 | 17 Jan. 1982 | 0 | | |
| 374-34P | C. woodii | Acetone post-infect | 1.0 | 14 Jan. 1982 | 17 Jan. 1982 | 0 | | |
| 374-34Q | C. woodii | Acetone post-infect | 0.1 | 14 Jan. 1982 | 17 Jan. 1982 | 0 | | |
| 374-35A | C. woodii | Acetone ppt | 1.0 | 14 Jan. 1982 | 17 Jan. 1982 | 0 | | |
| 374-35B | C. woodii | Acetone ppt | 0.1 | 14 Jan. 1982 | 17 Jan. 1982 | 0 | | |
| 374-35E | C. woodii | 1N NaOH | 0.01 | 14 Jan. 1982 | 17 Jan. 1982 | 5 | | |

TABLE 9

| Sample Number | Species | Extract purification | mg/ml Concentrate | Infection Start date | Reading 1 Date | Percent CPE |
|---|---|---|---|---|---|---|
| 374-35F | C. woodii | 1N NaOH ppt | na | 14 Jan. 1982 | 17 Jan. 1982 | 0 |
| 374-35G | C. woodii | 1N HCl | 0.01 | 14 Jan. 1982 | 17 Jan. 1982 | 0 |
| 374-35H | C. woodii | 1N HCl ppt | 0.01 | 14 Jan. 1982 | 17 Jan. 1982 | 5 |
| | HSV-1 | Control | $10^{-3}$ | 4 Jan. 1982 | 17 Jan. 1982 | 100 |
| 374-36A | C. woodii | 1N HCl 50,000 MW | 0.1 | 22 Jan. 1982 | 25 Jan. 1982 | 0 |
| 374-36B | C. woodii | 1N HCl 50,000 MW | 0.01 | 22 Jan. 1982 | 25 Jan. 1982 | 12 |
| 374-36C | C. woodii | 1N HCl 50,000 MW | 0.001 | 22 Jan. 1982 | 25 Jan. 1982 | 100 |
| 374-36D | C. woodii | 1N HCl 50-10,000 MW | 0.1 | 22 Jan. 1982 | 25 Jan. 1982 | 50 |
| 374-36E | C. woodii | 1N HCl 50-10,000 MW | 0.01 | 22 Jan. 1982 | 25 Jan. 1982 | 100 |
| 374-36F | C. woodii | 1N HCl 50-10,000 MW | 0.001 | 22 Jan. 1982 | 25 Jan. 1982 | 100 |
| 374-36G | C. woodii | 1N HCl 10,000 MW | 0.1 | 22 Jan. 1982 | 25 Jan. 1982 | 100 |
| 374-36H | C. woodii | 1N HCl 10,000 MW | 0.01 | 22 Jan. 1982 | 25 Jan. 1982 | 100 |
| 374-36I | C. woodii | 1N HCl 10,000 MW | 0.001 | 22 Jan. 1982 | 25 Jan. 1982 | 100 |
| 374-36J | C. woodii | 1N HCl 10,000 MW | 0.0001 | 22 Jan. 1982 | 25 Jan. 1982 | 100 |
| 374-36L | C. woodii | Chymotrypsin | 0.01 | 22 Jan. 1982 | 25 Jan. 1982 | 0 |
| 374-36N | C. woodii | β-xylosidase | 0.01 | 22 Jan. 1982 | 25 Jan. 1982 | 0 |
| 374-36P | C. woodii | βn-acetylglucosaminidase | 0.01 | 22 Jan. 1982 | 25 Jan. 1982 | 0 |
| 374-36Q | C. woodii | β-glucuronidase | 0.1 | 22 Jan. 1982 | 25 Jan. 1982 | 0 |
| 374-36R | C. woodii | β-glucuronidase | 0.01 | 22 Jan. 1982 | 25 Jan. 1982 | 5 |
| 374-37A | C. woodii | β-galactosidase | 0.1 | 27 Jan. 1982 | 31 Jan. 1982 | 5 |
| 374-37B | C. woodii | β-galactosidase | 0.01 | 27 Jan. 1982 | 31 Jan. 1982 | 40 |

TABLE 10

| Sample Number | Species | Extract purification | mg/ml Concentrate | Infection Start date | Reading 1 Date | Percent CPE | Reading 2 Date | Percent CPE |
|---|---|---|---|---|---|---|---|---|
| 374-37E | C. woodii | Periodate | 0.1 | 27 Jan. 1982 | 31 Jan. 1982 | 0 | | |
| 374-37F | C. woodii | Periodate | 0.01 | 27 Jan. 1982 | 31 Jan. 1982 | 10 | | |
| 374-37G | C. woodii | IOH- | 0.1 | 27 Jan. 1982 | 31 Jan. 1982 | 0 | | |
| 374-37H | C. woodii | IOH- | 0.01 | 27 Jan. 1982 | 31 Jan. 1982 | 2 | | |
| 374-37I | C. woodii | EtOH 300,000 MW | 0.01 | 27 Jan. 1982 | 31 Jan. 1982 | 0 | | |
| 374-37J | C. woodii | EtOH 300,000 MW | 0.001 | 27 Jan. 1982 | 31 Jan. 1982 | 5 | | |
| 374-37K | C. woodii | EtOH 300-100,000 | 0.01 | 27 Jan. 1982 | 31 Jan. 1982 | 50 | | |
| 374-37L | C. woodii | EtOH 300-100,000 | 0.001 | 27 Jan. 1982 | 31 Jan. 1982 | 50 | | |
| 374-37M | C. woodii | EtOH 100-50,000 | 0.01 | 27 Jan. 1982 | 31 Jan. 1982 | 100 | | |
| 374-37N | C. woodii | EtOH 100-50,000 | 0.001 | 27 Jan. 1982 | 31 Jan. 1982 | 100 | | |
| 374-37O | C. woodii | 1N HCl 300,000 MW | 0.01 | 27 Jan. 1982 | 31 Jan. 1982 | 10 | | |
| 374-37P | C. woodii | 1N HCl 300,000 MW | 0.001 | 27 Jan. 1982 | 31 Jan. 1982 | 90 | | |
| 374-37Q | C. woodii | 1N HCl 300-100,000 | 0.01 | 27 Jan. 1982 | 31 Jan. 1982 | 25 | | |
| 374-37R | C. woodii | 1N HCl 300-100,000 | 0.001 | 27 Jan. 1982 | 31 Jan. 1982 | 100 | | |
| 374-37S | C. woodii | 1N HCl 100-50,000 | 0.01 | 27 Jan. 1982 | 31 Jan. 1982 | 75 | | |
| 374-37T | C. woodii | 1N HCl 100-50,000 | 0.001 | 27 Jan. 1982 | 31 Jan. 1982 | 100 | | |
| 374-37U | C. woodii | EtOH ppt | 0.01 | 27 Jan. 1982 | 31 Jan. 1982 | 0 | | |
| 374-37V | C. woodii | EtOH ppt | 0.001 | 27 Jan. 1982 | 31 Jan. 1982 | 5 | | |
| | HSV-1 | Control | $10^{-3}$ | 27 Jan. 1982 | 31 Jan. 1982 | 100 | | |
| 374-39A | C. woodii | 1N HCl 4 hr 100° C. 300K | 0.01 | 4 Feb. 1982 | 7 Feb. 1982 | 100 | 11 Feb. 1982 | 100 |
| 374-39B | C. woodii | 1N HCl 4 hr 100° C. 300K | 0.001 | 4 Feb. 1982 | 7 Feb. 1982 | 100 | 11 Feb. 1982 | 100 |
| 374-39C | C. woodii | 1N HCl 24 hr 100-300K | 0.01 | 4 Feb. 1982 | 7 Feb. 1982 | 100 | 11 Feb. 1982 | 100 |
| 374-39D | C. woodii | 1N HCl 24 hr 100-300K | 0.001 | 4 Feb. 1982 | 7 Feb. 1982 | 100 | 11 Feb. 1982 | 100 |
| 374-39E | C. woodii | 1N HCl 24 hr 50-100K | 0.01 | 4 Feb. 1982 | 7 Feb. 1982 | 100 | 11 Feb. 1982 | 100 |

TABLE 10-continued

| Sample Number | Species | Extract purification | mg/ml Concentrate | Infection Start date | Reading 1 Date | Percent CPE | Reading 2 Date | Percent CPE |
|---|---|---|---|---|---|---|---|---|
| 374-39F | C. woodii | 1N HCl 24 hr 50–100K | 0.001 | 4 Feb. 1982 | 7 Feb. 1982 | 100 | 11 Feb. 1982 | 100 |
| 374-39G | C. woodii | 1N HCl 24 hr 100° C. 300K | 0.01 | 4 Feb. 1982 | 7 Feb. 1982 | 100 | 11 Feb. 1982 | 100 |
| 374-39H | C. woodii | 1N HCl 24 hr 100° C. 300K | 0.001 | 4 Feb. 1982 | 7 Feb. 1982 | 80 | 11 Feb. 1982 | 100 |
| 374-39I | C. woodii | 1N HCl 24 hr 100° C. 100–300K | 0.01 | 4 Feb. 1982 | 7 Feb. 1982 | 100 | 11 Feb. 1982 | 100 |

TABLE 11

| Sample Number | Species | Extract purification | mg/ml Concentrate | Infection Start date | Reading 1 Date | Percent CPE | Reading 2 Date | Percent CPE |
|---|---|---|---|---|---|---|---|---|
| 374-39J | C. woodii | 1N HCl 24 hr 100° C. 100–300K | 0.001 | 4 Feb. 1982 | 7 Feb. 1982 | 100 | 11 Feb. 1982 | 100 |
| 374-39K | C. woodii | 1N HCl 24 hr 100° C. 50–100K | 0.01 | 4 Feb. 1982 | 7 Feb. 1982 | 100 | 11 Feb. 1982 | 100 |
| 374-39L | C. woodii | 1N HCl 24 hr 100° C. 50–100K | 0.001 | 4 Feb. 1982 | 7 Feb. 1982 | 100 | 11 Feb. 1982 | 100 |
| 374-39M | C. woodii | 1N HCl 24 hr 100° C. 300K | 0.01 | 4 Feb. 1982 | 7 Feb. 1982 | 100 | 11 Feb. 1982 | 100 |
| 374-39N | C. woodii | 1N HCl 24 hr 100° C. 300K | 0.001 | 4 Feb. 1982 | 7 Feb. 1982 | 100 | 11 Feb. 1982 | 100 |
| 374-39O | C. woodii | 1N HCl 24 hr 100–300K | 0.01 | 4 Feb. 1982 | 7 Feb. 1982 | 80 | 11 Feb. 1982 | 100 |
| 374-39P | C. woodii | 1N HCl 24 hr 100–300K | 0.001 | 4 Feb. 1982 | 7 Feb. 1982 | 100 | 11 Feb. 1982 | 100 |
| 374-39Q | C. woodii | 1N HCl 24 hr 50–100K | 0.01 | 4 Feb. 1982 | 7 Feb. 1982 | 100 | 11 Feb. 1982 | 100 |
| 374-39R | C. woodii | 1N HCl 24 hr 50–100K | 0.001 | 4 Feb. 1982 | 7 Feb. 1982 | 100 | 11 Feb. 1982 | 100 |
| 374-39S | C. woodii | 6N HCl 4 hr 100° 300K | 0.01 | 4 Feb. 1982 | 7 Feb. 1982 | 100 | 11 Feb. 1982 | 100 |
| 374-39T | C. woodii | 6N HCl 4 hr 100° 300K | 0.001 | 4 Feb. 1982 | 7 Feb. 1982 | 80 | 11 Feb. 1982 | 100 |
| 374-39U | C. woodii | 6N HCl 4 hr 100° 300K | 0.01 | 4 Feb. 1982 | 7 Feb. 1982 | 100 | 11 Feb. 1982 | 100 |
| 374-39V | C. woodii | 6N HCl 4 hr 100° 300K | 0.001 | 4 Feb. 1982 | 7 Feb. 1982 | 100 | 11 Feb. 1982 | 100 |
| 374-39W | C. woodii | 1N HCl 24 hr 100° C. 50–100K | 0.01 | 4 Feb. 1982 | 7 Feb. 1982 | 100 | 11 Feb. 1982 | 100 |
| 374-39X | C. woodii | 1N HCl 24 hr 100° C. 50–100K | 0.001 | 4 Feb. 1982 | 7 Feb. 1982 | 100 | 11 Feb. 1982 | 100 |
| 374-39Y | C. woodii | Chondroitinase | 0.01 | 4 Feb. 1982 | 7 Feb. 1982 | 0 | 11 Feb. 1982 | Contaminated |
| 374-39Z | C. woodii | Chondroitinase | 0.001 | 4 Feb. 1982 | 7 Feb. 1982 | 0 | 11 Feb. 1982 | Contaminated |
| | HSV-1 | Control | $10^{-3}$ | 4 Feb. 1982 | 7 Feb. 1982 | 100 | 11 Feb. 1982 | 100 |
| 374-40A | C. woodii | 1N HCl 4 hr 100° C. ppt | na | 13 Feb. 1982 | 16 Feb. 1982 | 0 | | |
| 374-40B | C. woodii | 1N HCl 24 hr 100° C. ppt | na | 13 Feb. 1982 | 16 Feb. 1982 | 0 | | |
| 374-40C | C. woodii | 1N HCl 24 hr 100° C. ppt | na | 13 Feb. 1982 | 16 Feb. 1982 | 0 | | |
| 374-40D | C. woodii | 6N HCl 4 hr 100° C. ppt | na | 13 Feb. 1982 | 16 Feb. 1982 | 0 | | |
| 374-40E | C. woodii | 0.04N HCl 100° C. | 0.01 | 13 Feb. 1982 | 16 Feb. 1982 | 100 | | |
| 374-40F | C. woodii | 0.04N HCl 100° C. | 0.001 | 13 Feb. 1982 | 16 Feb. 1982 | 100 | | |
| 374-40G | C. woodii | Hyaluronidase 300K | 0.01 | 13 Feb. 1982 | 16 Feb. 1982 | 5 | | |
| 374-40H | C. woodii | Hyaluronidase 300K | 0.001 | 13 Feb. 1982 | 16 Feb. 1982 | 20 | | |
| 374-40I | C. woodii | Hyaluronidase 100–300K | 0.01 | 13 Feb. 1982 | 16 Feb. 1982 | 50 | | |
| 374-40J | C. woodii | Hyaluronidase 100–300K | 0.001 | 13 Feb. 1982 | 16 Feb. 1982 | 100 | | |
| 374-40K | C. woodii | Hyaluronidase 50–100K | 0.01 | 13 Feb. 1982 | 16 Feb. 1982 | 90 | | |
| 374-40L | C. woodii | Hyaluronidase 50–100K | 0.001 | 13 Feb. 1982 | 16 Feb. 1982 | 100 | | |

TABLE 12

| Sample Number | Species | Extract purification | mg/ml Concentrate | Infection Start date | Reading 1 Date | Percent CPE | Reading 2 Date | Percent CPE |
|---|---|---|---|---|---|---|---|---|
| 374-40M | C. woodii | Sulfatase | 0.01 | 13 Feb. 1982 | 16 Feb. 1982 | 5 | | |
| 374-40N | C. woodii | Sulfatase | 0.001 | 13 Feb. 1982 | 16 Feb. 1982 | 50 | | |
| 374-40O | C. woodii | EtOH ppt | 0.01 | 13 Feb. 1982 | 16 Feb. 1982 | 0 | | |
| 374-40P | C. woodii | EtOH ppt | 0.001 | 13 Feb. 1982 | 16 Feb. 1982 | 20 | | |
| 374-42G | C. woodii | 0.04N HCl 100° C. | 0.01 | 18 Feb. 1982 | 21 Feb. 1982 | 100 | | |
| 374-42H | C. woodii | 0.04N HCl 100° C. | 0.001 | 18 Feb. 1982 | 21 Feb. 1982 | 100 | | |
| 374-42I | C. woodii | Agar | 1.0 | 18 Feb. 1982 | 21 Feb. 1982 | 23 | | |
| 374-42J | C. woodii | Agar | 0.1 | 18 Feb. 1982 | 21 Feb. 1982 | 100 | | |
| 374-42K | C. woodii | Agar | 0.01 | 18 Feb. 1982 | 21 Feb. 1982 | 100 | | |
| 374-42L | C. woodii | Chondroitin | 1.0 | 18 Feb. 1982 | 21 Feb. 1982 | 35 | | |
| 374-42M | C. woodii | Chondroitin | 0.01 | 18 Feb. 1982 | 21 Feb. 1982 | 100 | | |
| 374-42N | C. woodii | Chondroitin | 0.01 | 18 Feb. 1982 | 21 Feb. 1982 | 100 | | |
| | HSV-1 | Control | $10^{-3}$ | 18 Feb. 1982 | 21 Feb. 1982 | 100 | | |
| | HSV-1 | Control | $10^{-4}$ | 18 Feb. 1982 | 21 Feb. 1982 | 12 | | |
| | HSV-1 | Control | $10^{-5}$ | 18 Feb. 1982 | 21 Feb. 1982 | 0 | | |

TABLE 13

| Sample Number | Species | Extract purification | mg/ml Concentrate | Infection Start date | Reading 1 Date | Percent CPE | Reading 2 Date | Percent CPE |
|---|---|---|---|---|---|---|---|---|
| 374-52F | C. woodii | Acetone/EtOH | 0.1 | 2 April 1982 | 5 April 1982 | 0 | 8 April 1982 | 0 |
| 374-52G | C. woodii | Acetone/EtOH | 0.01 | 2 April 1982 | 5 April 1982 | 8 | 8 April 1982 | 50 |
| 374-52H | C. woodii | Acetone/EtOH | 0.001 | 2 April 1982 | 5 April 1982 | 25 | 8 April 1982 | 80 |
| 374-55F | C. woodii | Protease | 0.1 | 8 April 1982 | 12 April 1982 | 0 | | |
| 374-55G | C. woodii | Protease | 0.01 | 8 April 1982 | 12 April 1982 | 0 | | |
| 374-55I | C. woodii | HCl | 0.01 | 8 April 1982 | 12 April 1982 | 15 | | |
| 374-55J | C. woodii | HCl | 0.001 | 8 April 1982 | 12 April 1982 | 45 | | |
| 374-55K | C. woodii | Acetone/EtOH | 0.1/ | | | | | |

TABLE 13-continued

| Sample Number | Species | Extract purification | mg/ml Concentrate | Infection Start date | Reading 1 Date | Percent CPE | Reading 2 Date | Percent CPE |
|---|---|---|---|---|---|---|---|---|
| 374-55L | C. woodii | Acetone/EtOH | HSV $10^{-1}$ | 8 April 1982 | 12 April 1982 | 0 | | |
| | | | 0.1/ HSV $10^{-2}$ | 8 April 1982 | 12 April 1982 | 0 | | |

TABLE 14

| Sample Number | Species | Extract purification | mg/ml Concentrate | Infection Start date | Reading 1 Date | Percent CPE | Reading 2 Date | Percent CPE |
|---|---|---|---|---|---|---|---|---|
| 374-55M | C. woodii | Acetone/EtOH | 0.1/ HSV $10^{-3}$ | 8 April 1982 | 12 April 1982 | 0 | | |
| 374-55N | C. woodii | Acetone HSV + 0.2 Filter | 0.1/ HSV $10^{-1}$ | 8 April 1982 | 12 April 1982 | 0 | | |
| 374-55O | C. woodii | Acetone HSV + 0.2 Filter | 0.1/ HSV $10^{-2}$ | 8 April 1982 | 12 April 1982 | 0 | | |
| 374-55P | C. woodii | Acetone HSV + 0.2 Filter | 0.1/ HSV $10^{-3}$ | 8 April 1982 | 12 April 1982 | 0 | | |
| | HSV-1 | Control | $10^{-3}$ | 8 April 1982 | 12 April 1982 | 100 | | |
| | HSV-1 | Control 0.2 Filter | $10^{-3}$ | 8 April 1982 | 12 April 1982 | 66 | | |

TABLE 15

| Sample Number | Species | Extract purification | mg/ml Concentrate | Infection Start date | Reading 1 Date | Percent CPE | Reading 2 Date | Percent CPE |
|---|---|---|---|---|---|---|---|---|
| 374-56A | C. woodii | Crude (solvent treated) | 0.1 | 17 April 1982 | 20 April 1982 | 7 | | |
| 374-56A | C. woodii | Crude (solvent treated) | 0.01 | 17 April 1982 | 20 April 1982 | 46 | | |
| 374-56A | C. woodii | Crude (solvent treated) | 0.001 | 17 April 1982 | 20 April 1982 | 100 | | |
| 374-56B | C. woodii | 20% EtOH ppt. | 0.1 | 17 April 1982 | 20 April 1982 | 0 | | |
| 374-56B | C. woodii | 20% EtOH ppt. | 0.01 | 17 April 1982 | 20 April 1982 | 0 | | |
| 374-56B | C. woodii | 20% EtOH ppt. | 0.001 | 17 April 1982 | 20 April 1982 | 24 | | |
| 374-57A | C. woodii | 33% EtOH ppt. | 0.01 | 17 April 1982 | 20 April 1982 | 4 | | |
| 374-57A | C. woodii | 33% EtOH ppt. | 0.001 | 17 April 1982 | 20 April 1982 | 12 | | |
| 374-57A | C. woodii | 33% EtOH ppt. | 0.0001 | 17 April 1982 | 20 April 1982 | 67 | | |
| 374-57B | C. woodii | Protease/EtOH ppt. | 0.01 | 17 April 1982 | 20 April 1982 | 5 | | |
| 374-57B | C. woodii | Protease/EtOH ppt. | 0.001 | 17 April 1982 | 20 April 1982 | 13 | | |
| 374-57B | C. woodii | Protease/EtOH ppt. | 0.0001 | 17 April 1982 | 20 April 1982 | 65 | | |
| | HSV-1 | Control | $10^{-3}$ | 17 April 1982 | 20 April 1982 | 100 | | |

TABLE 16

| Sample Number | Species | Extract purification | mg/ml Concentrate | Infection Start date | Reading 1 Date | Percent CPE |
|---|---|---|---|---|---|---|
| 374-57C | C. woodii | 1% Triton, high salts | 0.1 | 23 April 1982 | 26 April 1982 | 0 |
| 374-57C | C. woodii | 1% Triton, high salts | 0.01 | 23 April 1982 | 26 April 1982 | 4 |
| 374-57C | C. woodii | 1% Triton, high salts | 0.001 | 23 April 1982 | 26 April 1982 | 100 |
| 374-57E | C. woodii | Protease + TCA + EtOH | 0.1 | 23 April 1982 | 26 April 1982 | 0 |
| 374-57E | C. woodii | Protease + TCA + EtOH | 0.01 | 23 April 1982 | 26 April 1982 | 0 |
| 374-57E | C. woodii | Protease + TCA + EtOH | 0.001 | 23 April 1982 | 26 April 1982 | 12 |
| 374-57F | C. woodii | Protease + EtOH | 0.1 | 23 April 1982 | 26 April 1982 | 0 |
| 374-57F | C. woodii | Protease + EtOH | 0.01 | 23 April 1982 | 26 April 1982 | 8 |
| 374-57F | C. woodii | Protease + EtOH | 0.001 | 23 April 1982 | 26 April 1982 | 7 |
| 374-57G | C. woodii | 374-56A + TCA | 0.1 | 23 April 1982 | 26 April 1982 | 0 |
| 374-57G | C. woodii | 374-56A + TCA | 0.01 | 23 April 1982 | 26 April 1982 | 9 |
| 374-57G | C. woodii | 374-56A + TCA | 0.001 | 23 April 1982 | 26 April 1982 | 26 |
| 374-61A | C. woodii | 374-48 + TCA | 0.1 | 23 April 1982 | 26 April 1982 | 0 |
| 374-61A | C. woodii | 374-48 + TCA | 0.01 | 23 April 1982 | 26 April 1982 | 6 |
| 374-61A | C. woodii | 374-48 + TCA | 0.001 | 23 April 1982 | 26 April 1982 | 17 |
| | HSV-1 | Control | $10^{-3}$ | 23 April 1982 | 26 April 1982 | 100 |
| | Buffer | Neg. Control | 0 | 23 April 1982 | 26 April 1982 | 0 |

TABLE 17

| Sample Number | Species | Extract purification | mg/ml Concentrate | Infection Start date | Reading 1 Date | Percent CPE | Reading 2 Date | Percent CPE |
|---|---|---|---|---|---|---|---|---|
| 374-76A | C. woodii | TCA 37° C. Control | 0.1 | 9 May 1982 | 12 May 1982 | 0 | | |
| 374-76A | C. woodii | TCA 37° C. Control | 0.01 | 9 May 1982 | 12 May 1982 | 0 | | |
| 374-76A | C. woodii | TCA 37° C. Control | 0.001 | 9 May 1982 | 12 May 1982 | 6 | | |
| 374-76B | C. woodii | Protease TCA | 0.01 | 9 May 1982 | 12 May 1982 | 0 | | |
| 374-76B | C. woodii | Protease TCA | 0.001 | 9 May 1982 | 12 May 1982 | 2 | | |
| 374-76C | C. woodii | α-mannosidase | 0.1 | 9 May 1982 | 12 May 1982 | 0 | | |
| 374-76C | C. woodii | α-mannosidase | 0.01 | 9 May 1982 | 12 May 1982 | 0 | | |
| 374-76C | C. woodii | α-mannosidase | 0.001 | 9 May 1982 | 12 May 1982 | 5 | | |
| 374-76D | C. woodii | β-glucosidase | 0.01 | 9 May 1982 | 12 May 1982 | 1 | | |
| 374-76D | C. woodii | β-glucosidase | 0.001 | 9 May 1982 | 12 May 1982 | 28 | | |
| 374-76E | C. woodii | hyaluronidase | 0.1 | 9 May 1982 | 12 May 1982 | 0 | | |

TABLE 17-continued

| Sample Number | Species | Extract purification | mg/ml Concentrate | Infection Start date | Reading 1 Date | Percent CPE | Reading 2 Date | Percent CPE |
|---|---|---|---|---|---|---|---|---|
| 374-76E | C. woodii | hyaluronidase | 0.01 | 9 May 1982 | 12 May 1982 | 0 | | |
| 374-76E | C. woodii | hyaluronidase | 0.001 | 9 May 1982 | 12 May 1982 | 11 | | |
| 374-76F | C. woodii | sulfatase | 0.1 | 9 May 1982 | 12 May 1982 | 0 | | |
| 374-76F | C. woodii | sulfatase | 0.01 | 9 May 1982 | 12 May 1982 | 0 | | |
| 374-76G | C. woodii | α-glucosidase | 0.1 | 9 May 1982 | 12 May 1982 | 0 | | |
| 374-76G | C. woodii | α-glucosidase | 0.01 | 9 May 1982 | 12 May 1982 | 0 | | |
| 374-76G | C. woodii | α-glucosidase | 0.001 | 9 May 1982 | 12 May 1982 | 6 | | |
| 374-76I | C. woodii | TCA/EtOH | 0.1 | 9 May 1982 | 12 May 1982 | 0 | | |
| 374-76I | C. woodii | TCA/EtOH | 0.01 | 9 May 1982 | 12 May 1982 | 0 | | |
| 374-76J | C. woodii | CPC | 0.1 | 9 May 1982 | 12 May 1982 | 0 | | |
| 374-76J | C. woodii | CPC | 0.01 | 9 May 1982 | 12 May 1982 | 0 | | |
| 374-76J | C. woodii | CPC | 0.001 | 9 May 1982 | 12 May 1982 | 2 | | |
| | HSV-1 | Control | $10^{-3}$ | 9 May 1982 | 12 May 1982 | 100 | | |
| | HSV-1 | Control | $10^{-3}$ | 9 May 1982 | 12 May 1982 | 100 | | |
| | Buffer | Neg. Control | 0 | 9 May 1982 | 12 May 1982 | 0 | | |

TABLE 18

| Sample Number | Species | Extract purification | mg/ml Concentrate | Infection Start date | Reading 1 Date | Percent CPE | Reading 2 Date | Percent CPE |
|---|---|---|---|---|---|---|---|---|
| 374-95 | C. woodii | Acetone extract | 0.1 | 10 June | 13 June | 20 | | |
| 374-95 | C. woodii | Acetone extract | 0.01 | 10 June | 13 June | 90 | | |
| 374-95 | C. woodii | Acetone extract | 0.001 | 10 June | 13 June | 100 | | |
| 462-3A | C. woodii | Crude buffered | 0.1 | 10 June | 13 June | 2 | | |
| 462-3A | C. woodii | Crude buffered | 0.01 | 10 June | 13 June | 40 | | |
| 462-3A | C. woodii | Crude buffered | 0.001 | 10 June | 13 June | 85 | | |
| 462-3B | C. woodii | Crude triton | 0.1 | 10 June | 13 June | 2 | | |
| 462-3B | C. woodii | Crude triton | 0.01 | 10 June | 13 June | 40 | | |
| 462-3B | C. woodii | Crude triton | 0.001 | 10 June | 13 June | 90 | | |
| | HSV-1 | Control | $10^{-3}$ | 10 June | 13 June | 100 | | |
| 462-63 | C. woodii | Acetone extract | 10.0 | 15 Aug | 16 Aug | 0 | 17 Aug | 0 |
| 462-63 | C. woodii | Acetone extract | 1.0 | 15 Aug | 16 Aug | 6 | 17 Aug | 20 |
| 462-63 | C. woodii | Acetone extract | 0.1 | 15 Aug | 16 Aug | 24 | 17 Aug | 50 |
| 462-66 | C. woodii | Chloroform extract | 10.0 | 15 Aug | 16 Aug | 0 | 17 Aug | 0 |
| 462-66 | C. woodii | Chloroform extract | 1.0 | 15 Aug | 16 Aug | 0 | 17 Aug | 0 |
| 462-66 | C. woodii | Chloroform extract | 0.1 | 15 Aug | 16 Aug | 2 | 17 Aug | 20 |
| | HSV-1 | Control | $10^{-3}$ | 15 Aug | 16 Aug | 60 | 17 Aug | 90 |

TABLE 19

| Sample Number | Species | Extract purification | mg/ml Concentrate | Infection Start date | Reading 1 Date | Plaque Score |
|---|---|---|---|---|---|---|
| 462-15A | C. woodii | Crude buffered dialyzed | 0.1 | 18 June | 20 June | 17 |
| 462-15A | C. woodii | Crude buffered dialyzed | 0.01 | 18 June | 20 June | 104 |
| 462-15B | C. woodii | Triton dialyzed | 0.1 | 18 June | 20 June | 18 |
| 462-15B | C. woodii | Triton dialyzed | 0.01 | 18 June | 20 June | 112 |
| 462-10A | C. woodii | Water extract | 0.1 | 18 June | 20 June | 53 |
| 462-10A | C. woodii | Water extract | 0.01 | 18 June | 20 June | 134 |
| 462-18A | C. woodii | Water extract/Protease | 0.1 | 18 June | 20 June | 4 |
| 462-18A | C. woodii | Water extract/Protease | 0.01 | 18 June | 20 June | 60 |
| 462-18A | C. woodii | Water extract/Protease | 0.001 | 18 June | 20 June | 134 |
| 462-5A | C. woodii | Ethanol extract | 1.0 | 18 June | 20 June | 142 |
| 432-114 | C. woodii | Crude Triton/Protease | 0.1 | 18 June | 20 June | 0 |
| 432-114 | C. woodii | Crude Triton/Protease | 0.01 | 18 June | 20 June | 55 |
| 432-114 | C. woodii | Crude Triton/Protease | 0.001 | 18 June | 20 June | 135 |
| | HSV-1 | Control | $10^{-3}$ | 18 June | 20 June | 134 |

TABLE 20

| | | | Post-infection treatment | | | | | |
|---|---|---|---|---|---|---|---|---|
| Sample Number | Species | Extract purification | mg/ml Concentrate | Infection Start date | Reading 1 Date | Plaque Score | Reading 2 Date | Percent CPE |
| 462-10A | C. woodii | Water extract 1 | 1.0 | 20 July | 22 July | 4 | 24 July | 100 |
| 461-10A | C. woodii | Water extract 1 | 0.1 | 20 July | 22 July | 8 | 24 July | 100 |
| 462-10B | C. woodii | Water extract 2 | 1.0 | 20 July | 22 July | 1 | 24 July | 100 |
| 462-10B | C. woodii | Water extract 2 | 0.1 | 20 July | 22 July | 24 | 24 July | 100 |
| 462-10C | C. woodii | Water extract 3 | 1.0 | 20 July | 22 July | 0 | 24 July | 0 |
| 462-10C | C. woodii | Water extract 3 | 0.1 | 20 July | 22 July | 0 | 24 July | 70 |
| 462-28A | C. woodii | Water extract 1 | 1.0 | 23 July | 25 July | 17 | 27 July | 100 |
| 462-28A | C. woodii | Water extract 1 | 0.1 | 23 July | 25 July | 20 | 27 July | 100 |
| 462-28B | C. woodii | Water extract 2 | 1.0 | 23 July | 25 July | 0 | 27 July | 100 |
| 462-28B | C. woodii | Water extract 2 | 0.1 | 23 July | 25 July | 12 | 27 July | 70 |
| | HSV-1 | Control | $10^{-4}$ | | | 17 | | 100 |

TABLE 21

Test Number: 295   HERPESVIRUS ANIMAL INFECTIONS & ALGAL TREATMENT
Date Infected: February 22, 1982    Date Experiment Terminated: March 3, 1982
Virus: HSV   Type: II   Strain: Rapp   Lot Number: 2-1-24-80   Dilution: 1:20
Route of Infection: Intravaginal   Route of Treatment: Intravaginal
Animal Used: G. Pig   Sex: Female   Strain: Hartley-Albino   Weight: 235–325 Grams
Treatment Schedule: 2×/day Feb. 22, 23, 24, 25, 26, 1982
HSV-1 scored for skin lesions 0 to +4 per area;
HSV-2 scored for inflammation, vesiculation, discharge and necrosis 0 to +16 per animal

| Serial Number | Extract Treatment | A — Active N — Not Act. T — Toxic | % Conc. | Vehicle | pH | Number of Animals | Number of Areas | Daily Average Score | | | Final Average Score | Deaths Paralysis Total |
|---|---|---|---|---|---|---|---|---|---|---|---|---|
| EP 1013 | Ethanol ppt/2.5N NaCl | A | 1.5 | D | 6.0 | 5 | 5 | 6.4 | 8.4 | 6.0 | 6.9 | 1/5 |
| EP 1014 | BSA + Protease Control | N | 2.5 | D | 7.0 | 5 | 5 | 10.0 | 12.25 | 14.5 | 12.25 | 1/5 |
| 17443 | PFA | A | 1.0 | D | 6.7 | 5 | 5 | 2.2 | 3.0 | 3.8 | 3.00 | 0/5 |
| Control | — | — | — | D | 6.7 | 5 | 5 | 10.2 | 12.0 | 12.75 | 11.65 | 1/5 |

TABLE 22

Test Number: 296   HERPEVIRUS ANIMAL INFECTIONS & ALGAL TREATMENT
Date Infected: March 1, 1982   Date Experiment Terminated: March 20, 1982
Virus: HSV   Type: II   Strain: Rapp   Lot Number: 2-1-24-80   Dilution: 1:20
Route of Infection: Intravaginal   Route of Treatment: Intravaginal
Animal Used: G. Pig   Sex: Female   Strain: Hartley-Albino   Weight: 275–325 Grams
Treatment Schedule: 2×/day March 1,2,3,4,5, 1982 Total of 8 Treatments No
HSV-1 scored for skin lesions 0 to +4 per area; HSV-2 scored for inflammation, vesiculation, discharge and necrosis 0 to +16 per animal.

| Serial Number | Extract Treatment | A—Active N—Not Act. T—Toxic | % Conc. | Vehicle | pH | Number of Animals | Number of Areas | Daily Average Score | | | Final Average Score | Deaths Paralysis Total |
|---|---|---|---|---|---|---|---|---|---|---|---|---|
| EP 1008 | Triton extracted | A | 1.0 | D | 6.7 | 5 | 5 | 4.4 | 3.6 | 4.2 | 4.06 | 0/5 |
| EP 1019 | Protease treated | A | 0.5 | D | 7.0 | 4 | 4 | 5.0 | 5.0 | 5.25 | 5.08 | 0/4 |
| 17443 | PFA | A | 1.0 | D | 6.7 | 3 | 3 | 2.67 | 2.67 | 3.33 | 2.89 | 0/3 |
| Control | — | — | — | D | 7.0 | 4 | 4 | 11.0 | 11.75 | 8.0 | 10.25 | 2/4 |

TABLE 23

Test Number: 292   HERPESVIRUS ANIMAL INFECTIONS & ALGAL TREATMENT
Date Infected: February 1, 1982   Date Experiment Terminated: February 10, 1982
Virus: HSV   Type: I   Strain: Stohr   Lot Number: 1-5-1-81   Dilution: 1:05
Route of Infection: Cutaneous   Route of Treatment: Topical
Animal Used: G. Pig   Sex: Female   Strain: Hartley-Albino   Weight: 275–325 Grams
Treatment Schedule 2×/day Feb. 1,2,3,4,5, 1982 Total of 8 Treatments No
HSV-1 scored for skin lesions 0 to +4 per area; HSV-2 scored for inflammation, vesiculation, discharge and necrosis 0 to +16 per animal.

| Serial Number | Extract Treatment | A—Active N—Not Act. T—Toxic | % Conc. | Vehicle | pH | Number of Animals | Number of Areas | Daily Average Score | | | Final Average Score | Deaths Paralysis Total |
|---|---|---|---|---|---|---|---|---|---|---|---|---|
| EP 1009 | Crude | N | 2.0 | D | 6.5 | 4 | 16 | 3.06 | 3.06 | 2.56 | 2.89 | 0/4 |
| EP 1010 | Crude | N | 2.0 | D | 5.0 | 4 | 16 | 2.75 | 2.63 | 2.38 | 2.59 | 0/4 |
| EP 1011 | Biobead | N | 2.0 | D | 5.0 | 4 | 16 | 3.31 | 2.75 | 2.50 | 2.85 | 0/4 |
| EP 1012 | Acetone ppt | N | 2.0 | D | 6.0 | 4 | 16 | 3.25 | 3.00 | 2.63 | 2.96 | 0/4 |
| EP 1013 | Ethanol ppt | N | 2.0 | D | 6.5 | 4 | 16 | 3.56 | 3.31 | 2.81 | 3.23 | 0/4 |
| EP 1014 | BSA + Protease control | N | 2.0 | D | 6.5 | 4 | 16 | 3.00 | 2.82 | 2.31 | 2.71 | 0/4 |
| EP 1019 | Protease | N | 1.0 | D | 6.7 | 4 | 16 | 3.06 | 2.81 | 2.82 | 2.89 | 0/4 |
| 17443 | Pfa | A | 0.50 | D | 6.7 | 2 | 8 | .63 | .63 | .63 | .63 | 0/2 |
| Control | — | — | — | D | 6.7 | 4 | 16 | 3.06 | 2.69 | 2.50 | 2.75 | 0/4 |

TABLE 24

Test Number: 302   HERPESVIRUS ANIMAL INFECTIONS & ALGAL TREATMENT
Date Infected: April 19, 1982   Date Experiment Terminated: April 28, 1982
Virus: HSV   Type: II   Strain: Rapp   Lot Number: 2-1-24-80   Dilution: 1:20
Route of Infection: Intravaginal   Route of Treatment: Intravaginal
Animal Used: G. Pig   Sex: Female   Strain: Hartley-Albino   Weight: 275–325 Grams
Treatment Schedule 2×/day April 19-20-21-22-23-1982
HSV-1 scored for skin lesions 0 to +4 per area; HSV-2 scored for inflammation, vesiculation, discharge and necrosis 0 to +16 per animal.

| Serial Number | Extract Treatment | A—Active N—Not Act. T—Toxic | % Conc. | Vehicle | pH | Number of Animals | Number of Areas | Daily Average Score | | | Final Average Score | Deaths Paralysis Total |
|---|---|---|---|---|---|---|---|---|---|---|---|---|
| EP 1020 | XM 300 1N HCl | N | 1.0 | D | 6.2 | 5 | 5 | 6.6 | 9.4 | 9.6 | 8.53 | 0/5 |
| EP 1021 | XM 300 EtOH (From EP1012) | N | 1.0 | D | 6.0 | 5 | 5 | 11.2 | 13.8 | 15.7 | 13.6 | 2/5 |

TABLE 24-continued

| Serial Number | Extract Treatment | A—Active N—Not Act. T—Toxic | % Conc. | Vehicle | pH | Number of Animals | Number of Areas | Daily Average Score | | | Final Average Score | Deaths Paralysis Total |
|---|---|---|---|---|---|---|---|---|---|---|---|---|
| EP 1022 | Protease | N | 1.0 | D | 6.2 | 5 | 5 | 8.4 | 10.8 | 10.6 | 9.93 | 0/5 |
| EP 1023 | CPC | N | 1.5 | D | 6.0 | 5 | 5 | 10.8 | 12.0 | 10.0 | 10.9 | 2/5 |
| 17443 | Pfp | A | 1.0 | D | 6.5 | 5 | 5 | 2.2 | 2.2 | 4.0 | 2.8 | 0/5 |
| Control | — | — | — | D | 6.5 | 5 | 5 | 10.0 | 11.0 | 11.3 | 10.8 | 2/5 |

TABLE 25

Test Number: 304  HERPESVIRUS ANIMAL INFECTIONS & ALGAL TREATMENT
Date Infected: May 19, 1982  Date Experiment Terminated: May 12, 1982
Virus: HSV  Type: I  Strain: Stohr  Lot Number: 1-5-1-81  Dilution: 1:5
Route of Infection: Cutaneous  Route of Treatment: Topical
Animal Used: G. Pig  Sex: Female  Strain: Hartley-Albino  Weight: 275–325 Grams
Treatment Schedule 2×/day May 19-20-21-22-23-1982
HSV-1 scored for skin lesions 0 to +4 per area; HSV-2 scored for inflammation, vesiculation, discharge and necrosis 0 to +16 per animal.

| Serial Number | Extract Treatment | A—Active N—Not Act. T—Toxic | % Conc. | Vehicle | pH | Number of Animals | Number of Areas | Daily Average Score | | | Final Average Score | Deaths Paralysis Total |
|---|---|---|---|---|---|---|---|---|---|---|---|---|
| EP 1020 | XM 300 1N HCl | N | 1.0 | D | 6.5 | 4 | 16 | 3.44 | 3.00 | 2.69 | 3.04 | 0/4 |
| EP 1021 | XM 300 EtOH | N | 1.0 | D | 6.5 | 4 | 16 | 3.44 | 2.94 | 2.44 | 2.94 | 0/4 |
| EP 1022 | Protease | N | 1.0 | D | 6.5 | 4 | 16 | 3.63 | 3.44 | 2.81 | 3.29 | 0/4 |
| EP 1023 | CPC | N | 1.0 | D | 6.5 | 4 | 16 | 3.44 | 2.81 | 2.63 | 2.96 | 0/4 |
| 17443 | Pfa | A | 0.50 | D | 6.5 | 2 | 8 | .38 | .25 | .25 | .29 | 0/2 |
| Control | — | — | — | D | 6.5 | 4 | 16 | 3.31 | 3.19 | 2.81 | 3.10 | 1/4 |

TABLE 26

Test Number: 305  HERPESVIRUS ANIMAL INFECTIONS & ALGAL TREATMENT
Date Infected: May 17, 1982  Date Experiment Terminated: May 26, 1982
Virus: HSV  Type: II  Strain: Rapp  Lot Number: 2-1-24-80  Dilution: 1:20
Route of Infection: Intravaginal  Route of Treatment: Intraperitoneal
Animal Used: G. Pig  Sex: Female  Strain: Hartley-Albino  Weight: 275–325 Grams
Treatment Schedule 2×/day May 17-18-19-20-21-1982
HSV-1 scored for skin lesions 0 to +4 per area; HSV-2 scored for inflammation, vesiculation, discharge and necrosis 0 to +16 per animal.

| Serial Number | Extract Treatment | A—Active N—Not Act. T—Toxic | % Conc. | Vehicle | pH | Number of Animals | Number of Areas | Daily Average Score | | | Final Average Score | Deaths Paralysis Total |
|---|---|---|---|---|---|---|---|---|---|---|---|---|
| EP 1021 | XM 300 EtOH | N | 2.0 | 5A | 6.0 | 5 | 5 | 8.4 | 10.6 | 12.8 | 10.6 | 0/5 |
| 17443 | Pfa | A | 0.5 | D | 6.5 | 5 | 5 | .80 | .80 | .80 | .80 | 0/5 |
| Control | — | — | — | D | 6.5 | 5 | 5 | 8.4 | 9.8 | 11.6 | 9.93 | 2/5 |

*374-66B - G. pigs inoc. Ip twice with 2.0% sol. on May 17 + 19-1982

TABLE 27

Test Number: 306  HERPESVIRUS ANIMAL INFECTIONS & ALGAL TREATMENT
Date Infected: May 24, 1982  Date Experiment Terminated: June 2, 1982
Virus: HSV  Type: II  Strain: Rapp  Lot Number: 2-1-24-80  Dilution: 1:20
Route of Infection: Intravaginal  Route of Treatment: Intravaginal
Animal Used: G. Pig  Sex: Female  Strain: Hartley-Albino  Weight: 275–325 Grams
Treatment Schedule May 24-25-26-27-28-1982
HSV-1 scored for skin lesions 0 to +4 per area; HSV-2 scored for inflammation, vesiculation, discharge and necrosis 0 to +16 per animal.

| Serial Number | Extract Treatment | A—Active N—Not Act. T—Toxic | % Conc. | Vehicle | pH | Number of Animals | Number of Areas | Daily Average Score | | Final Average Score | Deaths Paralysis Total |
|---|---|---|---|---|---|---|---|---|---|---|---|
| EP 1025 | Solvent treated/Protease | N | 4.0 | D | 6.5 | 5 | 5 | 7.6 | 9.6 | 8.6 | 0/5 |
| EP 1026 | Solvent treated CPC | N | 4.0 | D | 6.5 | 5 | 5 | 10.8 | 12.5 | 11.7 | 1/5 |
| EP 1027 | Solvent treated HCl | N | 4.0 | D | 5.7 | 5 | 5 | 10.2 | 11.6 | 10.9 | 0/5 |
| EP 1028 | Solvent treated TCA | N | 4.0 | D | 6.0 | 5 | 5 | 11.0 | 13.0 | 12.0 | 0/5 |
| 17443 | Pfa | A | 1.0 | D | 6.5 | 5 | 5 | .60 | 1.2 | 0.9 | 0/5 |
| Control | — | — | — | D | 6.7 | 5 | 5 | 5.6 | 6.4 | 6.0 | 0/5 |

TABLE 28

Test Number: 307  HERPESVIRUS ANIMAL INFECTIONS & ALGAL TREATMENT
Date Infected: June 7, 1982  Date Experiment Terminated: June 16, 1982
Virus: HSV  Type: II  Strain: Rapp  Lot Number: 2-1-24-80  Dilution: 1:20
Route of Infection: Intravaginal  Route of Treatment: Intravaginal
Animal Used: G. Pig  Sex: Female  Strain: Hartley-Albino  Weight: 275–325 Grams
Treatment Schedule June 7-8-9-10-11-1982 2×/Day
HSV-1 scored for skin lesions 0 to +4 per area; HSV-2 scored for inflammation, vesiculation, discharge and necrosis 0 to +16 per animal.

| Serial | A—Active N—Not Act. | % | Number of | Number of | Final Average | Deaths Paralysis |